(12) United States Patent
Bakos et al.

(10) Patent No.: US 12,082,834 B2
(45) Date of Patent: Sep. 10, 2024

(54) TISSUE CUSHION ADJUNCT WITH STAPLE LEG SUPPORT FEATURES FOR SURGICAL STAPLER END EFFECTOR

(71) Applicant: Cilag GmbH International, Zug (CH)

(72) Inventors: Gregory J. Bakos, Mason, OH (US); Christopher Q. Seow, Cincinnati, OH (US); Jason M. Rector, Maineville, OH (US); Mark S. Zeiner, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/704,083

(22) Filed: Mar. 25, 2022

(65) Prior Publication Data

US 2023/0320742 A1 Oct. 12, 2023

(51) Int. Cl.
*A61B 17/072* (2006.01)
*A61B 17/00* (2006.01)
(Continued)

(52) U.S. Cl.
CPC ........ *A61B 17/29* (2013.01); *A61B 17/00234* (2013.01); *A61B 17/0684* (2013.01);
(Continued)

(58) Field of Classification Search
CPC .......................................... A61B 2017/07271
See application file for complete search history.

(56) References Cited

U.S. PATENT DOCUMENTS

| 5,810,855 A | 9/1998 | Rayburn et al. |
| 7,380,696 B2 | 6/2008 | Shelton, IV et al. |

(Continued)

FOREIGN PATENT DOCUMENTS

| EP | 2090248 A2 | 8/2009 |
| EP | 3150134 A1 | 4/2017 |

(Continued)

OTHER PUBLICATIONS

International Search Report and Written Opinion dated Aug. 2, 2023, for International Application No. PCT/IB2023/052793, 20 pages.

(Continued)

*Primary Examiner* — Thanh K Truong
*Assistant Examiner* — Patrick B Fry
(74) *Attorney, Agent, or Firm* — Frost Brown Todd LLP

(57) ABSTRACT

A surgical instrument includes an end effector including a first jaw having a plurality of pockets and a second jaw. The first and second jaws are operable to clamp tissue therebetween. The surgical instrument also includes a stapling assembly supported by the second jaw of the end effector. The stapling assembly includes a deck, a plurality of staple openings extending through the deck, and a plurality of staples slidably housed within corresponding staple openings. Each staple has a respective pair of legs configured to be driven into contact with a corresponding pocket. The surgical instrument further includes a plurality of staple leg constraints. Each staple leg constraint is aligned with and extends at least partially across a corresponding staple opening for guiding a respective leg of the corresponding staple toward the corresponding pocket.

20 Claims, 21 Drawing Sheets

(51) Int. Cl.
*A61B 17/068* (2006.01)
*A61B 17/29* (2006.01)

(52) U.S. Cl.
CPC .. *A61B 17/072* (2013.01); *A61B 2017/07214* (2013.01); *A61B 2017/07242* (2013.01); *A61B 2017/2927* (2013.01)

(56) References Cited

U.S. PATENT DOCUMENTS

| | | | |
|---|---|---|---|
| 7,845,533 | B2 | 12/2010 | Marczyk et al. |
| 8,034,396 | B2 | 10/2011 | Kapiamba et al. |
| 8,210,411 | B2 | 7/2012 | Yates et al. |
| 8,408,439 | B2 | 4/2013 | Huang et al. |
| 8,453,914 | B2 | 6/2013 | Laurent et al. |
| 9,186,142 | B2 | 11/2015 | Fanelli et al. |
| 9,271,706 | B2 | 3/2016 | Stopek et al. |
| 9,364,233 | B2 | 6/2016 | Alexander, III et al. |
| 9,517,065 | B2 | 12/2016 | Simms et al. |
| 9,622,746 | B2 | 4/2017 | Simms et al. |
| 9,649,110 | B2 | 5/2017 | Parihar et al. |
| 9,717,497 | B2 | 8/2017 | Zerkle et al. |
| 9,795,379 | B2 | 10/2017 | Leimbach et al. |
| 9,808,248 | B2 | 11/2017 | Hoffman |
| 9,839,421 | B2 | 12/2017 | Zerkle et al. |
| 9,907,554 | B2 | 3/2018 | Morgan et al. |
| 10,092,292 | B2 | 10/2018 | Boudreaux et al. |
| 10,166,023 | B2 | 1/2019 | Vendely et al. |
| 10,349,939 | B2 | 7/2019 | Shelton, IV et al. |
| 10,426,481 | B2 | 10/2019 | Aronhalt et al. |
| 10,441,285 | B2 | 10/2019 | Shelton, IV et al. |
| 10,524,788 | B2 | 1/2020 | Vendely et al. |
| 10,568,621 | B2 | 2/2020 | Shelton, IV et al. |
| 10,588,623 | B2 | 3/2020 | Schmid et al. |
| 10,624,861 | B2 | 4/2020 | Widenhouse et al. |
| 10,639,039 | B2 | 5/2020 | Vendely et al. |
| 10,667,808 | B2 | 6/2020 | Baxter, III et al. |
| 10,758,398 | B2 | 9/2020 | Murthy Aravalli et al. |
| 10,945,731 | B2 | 3/2021 | Baxter, III et al. |
| 10,966,722 | B2 | 4/2021 | Shelton, IV et al. |
| 10,987,107 | B2 | 4/2021 | Sgroi, Jr. et al. |
| 11,058,425 | B2 | 7/2021 | Widenhouse et al. |
| 11,382,625 | B2 * | 7/2022 | Huitema .......... A61B 17/07207 |
| 11,660,093 | B2 | 5/2023 | Bakos et al. |
| 11,857,190 | B2 | 1/2024 | Strang et al. |
| 2002/0165563 | A1 | 11/2002 | Grant et al. |
| 2005/0263562 | A1 | 12/2005 | Shelton et al. |
| 2009/0020584 | A1 * | 1/2009 | Soltz .................... A61B 17/068 227/175.1 |
| 2009/0206143 | A1 | 8/2009 | Huitema et al. |
| 2010/0331880 | A1 | 12/2010 | Stopek et al. |
| 2011/0077629 | A1 | 3/2011 | Tanaka et al. |
| 2012/0080336 | A1 | 4/2012 | Shelton, IV et al. |
| 2012/0080498 | A1 | 4/2012 | Shelton, IV et al. |
| 2012/0080503 | A1 | 4/2012 | Woodard, Jr. et al. |
| 2012/0083836 | A1 | 4/2012 | Shelton, IV et al. |
| 2012/0125792 | A1 | 5/2012 | Cassivi |
| 2012/0136345 | A1 | 5/2012 | Takashino |
| 2012/0241492 | A1 | 9/2012 | Shelton, IV et al. |
| 2012/0241503 | A1 | 9/2012 | Baxter, III et al. |
| 2012/0241505 | A1 | 9/2012 | Alexander, III et al. |
| 2013/0146641 | A1 | 6/2013 | Shelton, IV et al. |
| 2013/0146643 | A1 | 6/2013 | Schmid et al. |
| 2013/0153635 | A1 | 6/2013 | Hodgkinson |
| 2013/0214030 | A1 | 8/2013 | Aronhalt et al. |
| 2013/0221062 | A1 | 8/2013 | Hodgkinson |
| 2013/0256376 | A1 | 10/2013 | Barton et al. |
| 2014/0131419 | A1 | 5/2014 | Bettuchi |
| 2014/0158741 | A1 | 6/2014 | Woodard, Jr. et al. |
| 2014/0166721 | A1 | 6/2014 | Stevenson et al. |
| 2014/0209658 | A1 | 7/2014 | Skalla et al. |
| 2014/0224686 | A1 | 8/2014 | Aronhalt et al. |
| 2014/0291382 | A1 | 10/2014 | Lloyd et al. |
| 2015/0136831 | A1 | 5/2015 | Baxter, III et al. |
| 2015/0196296 | A1 | 7/2015 | Swayze et al. |
| 2015/0196348 | A1 | 7/2015 | Yates et al. |
| 2015/0282809 | A1 | 10/2015 | Shelton, IV et al. |
| 2016/0278764 | A1 | 9/2016 | Shelton, IV et al. |
| 2016/0278765 | A1 | 9/2016 | Shelton, IV et al. |
| 2016/0278774 | A1 | 9/2016 | Shelton, IV et al. |
| 2017/0055981 | A1 | 3/2017 | Vendely et al. |
| 2017/0055986 | A1 | 3/2017 | Harris et al. |
| 2017/0086838 | A1 | 3/2017 | Harris et al. |
| 2017/0086841 | A1 | 3/2017 | Vendely et al. |
| 2017/0086845 | A1 | 3/2017 | Vendely et al. |
| 2017/0119390 | A1 | 5/2017 | Schellin et al. |
| 2017/0119392 | A1 | 5/2017 | Shelton, IV et al. |
| 2018/0103952 | A1 | 4/2018 | Aronhalt et al. |
| 2018/0235624 | A1 | 8/2018 | Shelton, IV et al. |
| 2018/0235626 | A1 | 8/2018 | Shelton, IV et al. |
| 2019/0008518 | A1 | 1/2019 | Sgroi, Jr. et al. |
| 2019/0200978 | A1 | 7/2019 | Shelton, IV et al. |
| 2019/0269402 | A1 * | 9/2019 | Murray ................ A61B 17/068 |
| 2019/0298338 | A1 | 10/2019 | Vendely et al. |
| 2019/0314016 | A1 | 10/2019 | Huitema et al. |
| 2019/0314018 | A1 * | 10/2019 | Huitema ............ A61B 17/0644 |
| 2020/0205825 | A1 | 7/2020 | Vendely et al. |
| 2020/0305963 | A1 | 10/2020 | Wagner et al. |
| 2020/0390944 | A1 | 12/2020 | Williams et al. |
| 2021/0128129 | A1 | 5/2021 | George et al. |
| 2022/0061843 | A1 | 3/2022 | Vendely et al. |
| 2022/0160360 | A1 | 5/2022 | Harris et al. |
| 2022/0313247 | A1 | 10/2022 | Shelton, IV et al. |
| 2023/0301656 | A1 | 9/2023 | Seow et al. |
| 2023/0301657 | A1 | 9/2023 | Zeiner et al. |
| 2023/0301674 | A1 | 9/2023 | Rector et al. |
| 2023/0301675 | A1 | 9/2023 | Seow et al. |

FOREIGN PATENT DOCUMENTS

| | | | |
|---|---|---|---|
| EP | 3150142 | A2 | 4/2017 |
| EP | 3162384 | A1 | 5/2017 |
| EP | 3363387 | A1 | 8/2018 |
| EP | 3424441 | A2 | 1/2019 |
| EP | 3530213 | A2 | 8/2019 |
| EP | 3791802 | A1 | 3/2021 |
| EP | 3791805 | A1 | 3/2021 |
| EP | 3791806 | A1 | 3/2021 |

OTHER PUBLICATIONS

International Search Report and Written Opinion dated Jul. 31, 2023, for International Application No. PCT/IB2023/052804, 21 pages.
International Search Report and Written Opinion dated Aug. 7, 2023, for International Application No. PCT/IB2023/052805, 21 pages.
International Search Report and Written Opinion dated Aug. 9, 2023, for International Application No. PCT/IB2023/052809, 20 pages.
International Search Report and Written Opinion dated Jun. 20, 2023, for International Application No. PCT/IB2023/052810, 16 pages.

* cited by examiner

TISSUE CUSHION ADJUNCT WITH STAPLE LEG SUPPORT FEATURES FOR SURGICAL STAPLER END EFFECTOR

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
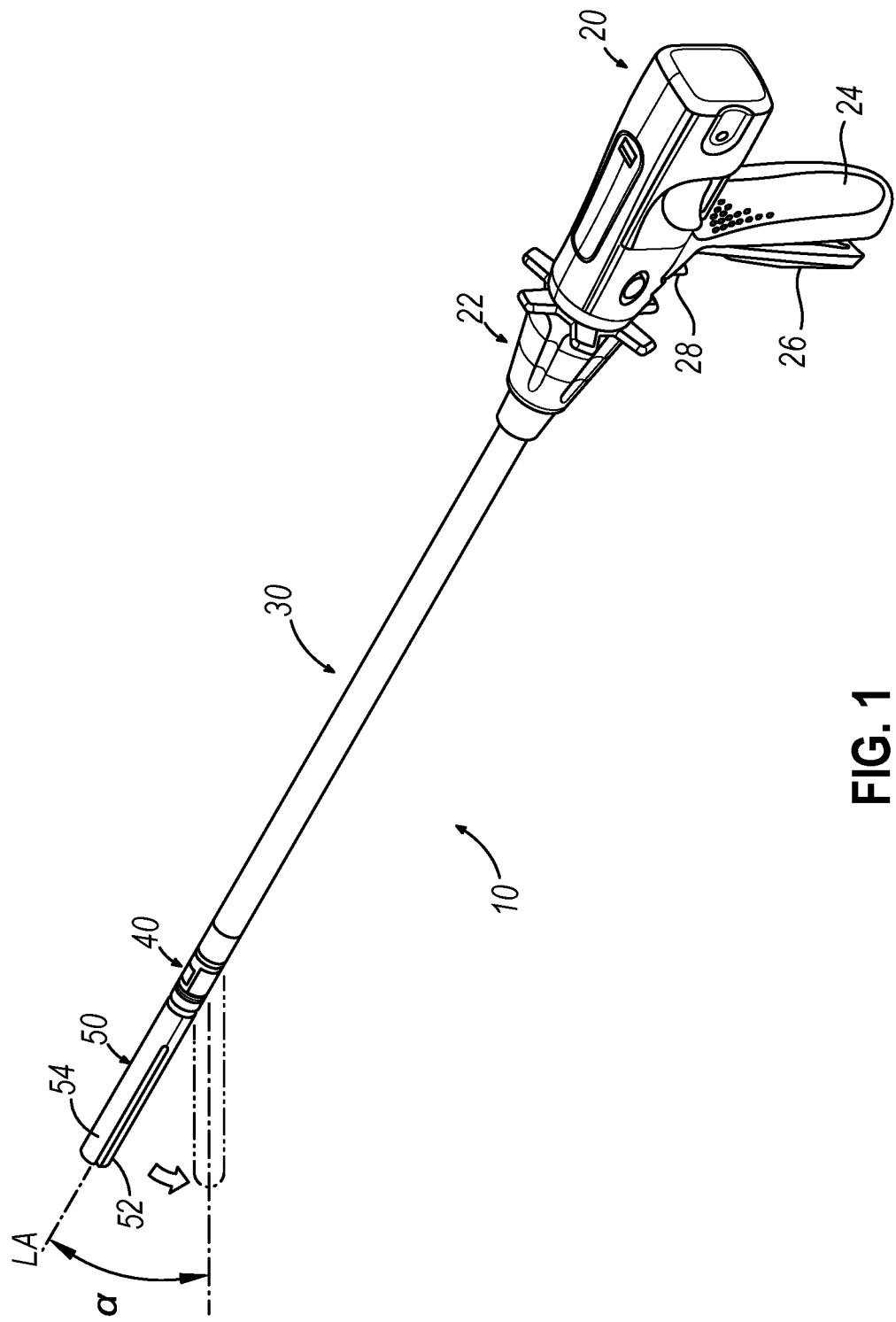
FIG. 1 depicts a perspective view of an exemplary surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. EXEMPLARY SURGICAL STAPLER

Figure 2:
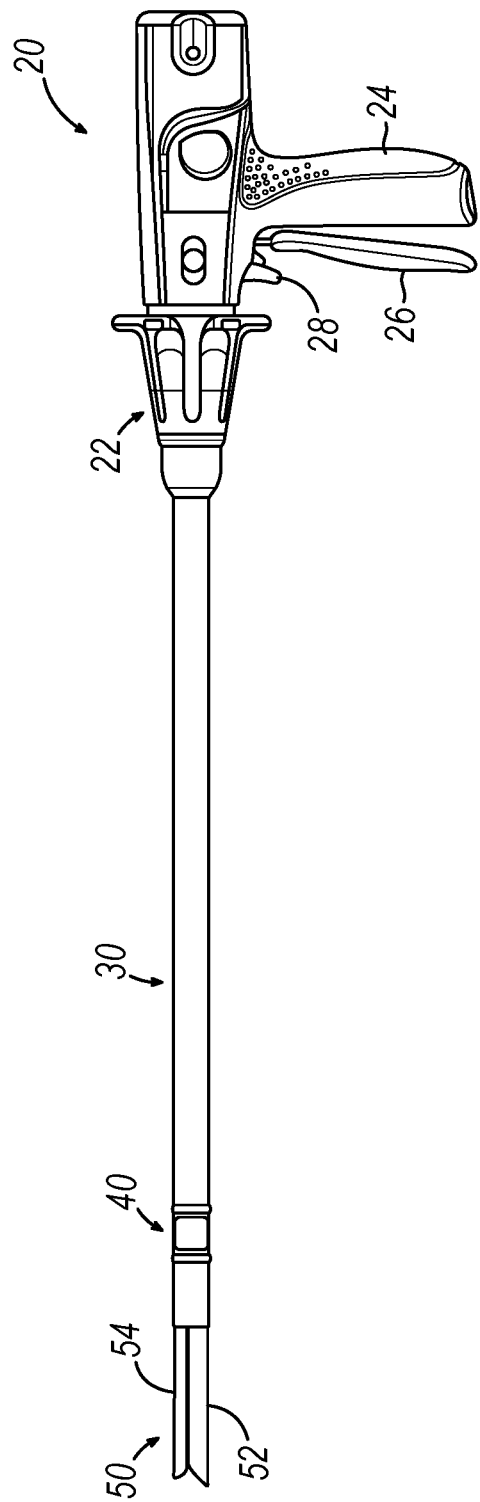
FIG. 2 depicts a side elevational view of the surgical stapler of FIG. 1.

FIGS. 1-6 show an exemplary surgical stapler (10) that is sized for insertion through a trocar cannula or an incision (e.g., thoracotomy, etc.) to a surgical site in a patient for performing a surgical procedure. As shown in FIGS. 1 and 2, surgical stapler (10) of the present example includes a proximal body in the form of a handle assembly (20), a shaft assembly (30) extending distally from handle assembly (20) and terminating at an articulation joint (40), and an end effector (50) coupled with the distal end of shaft assembly (30) via articulation joint (40). Articulation joint (40) is configured to enable lateral deflection, either actively or passively, of end effector (50) relative to a longitudinal axis (LA) of shaft assembly (30) to a desired angle (α) via actuation of an articulation control feature (22) of handle assembly (20).

Figure 3:
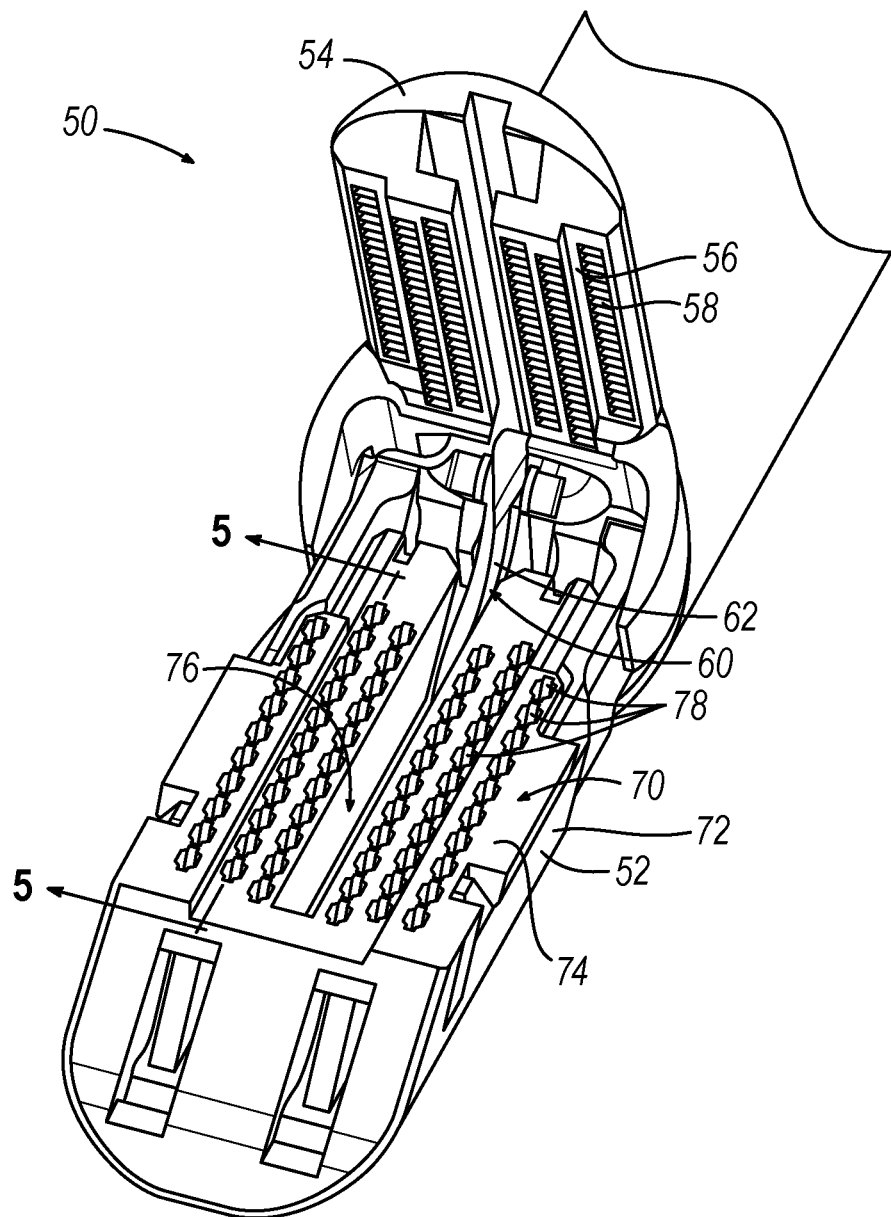
FIG. 3 depicts a perspective view of an end effector of the surgical stapler of FIG. 1 in an open state.
Figure 4:
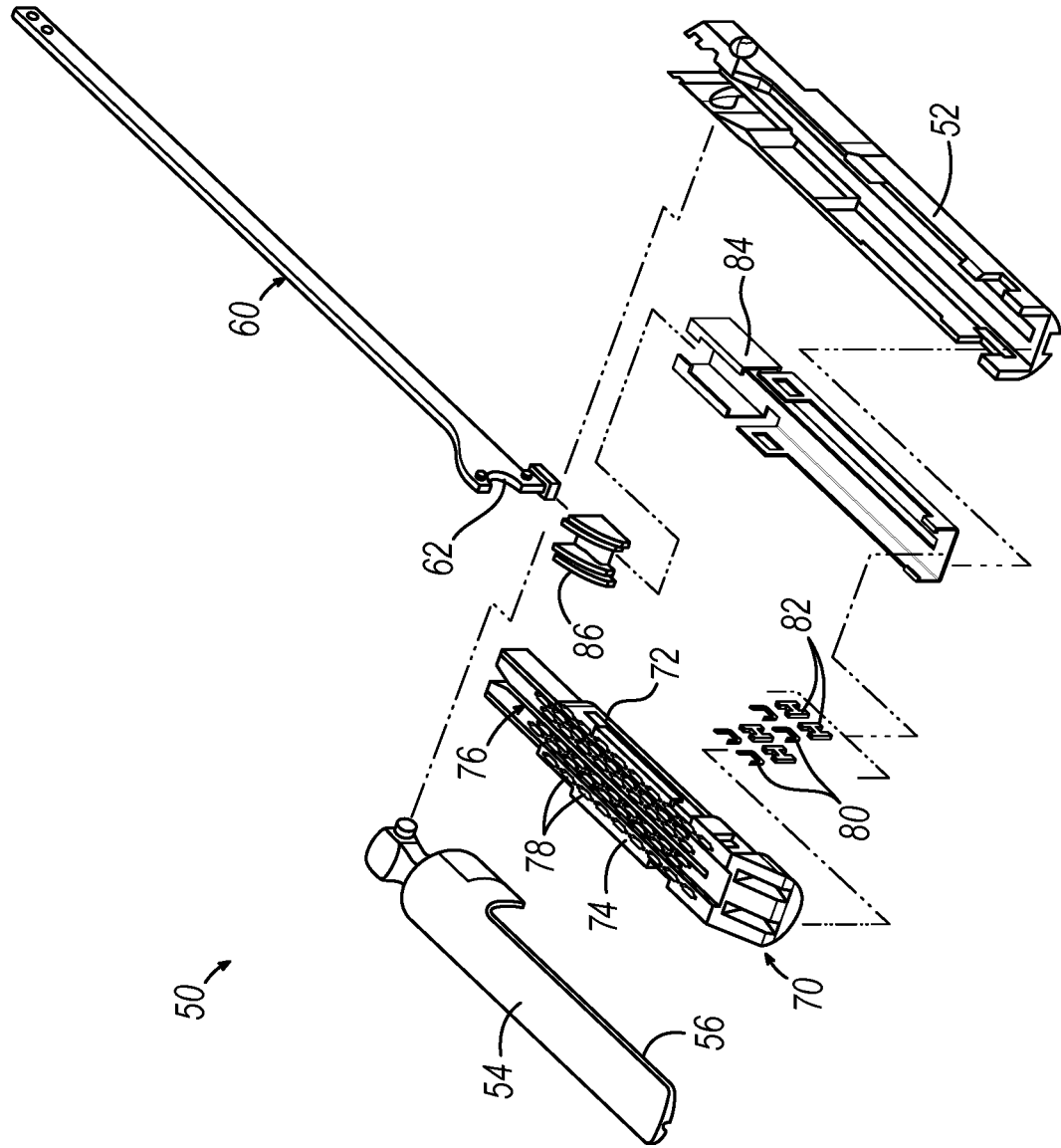
FIG. 4 depicts an exploded perspective view of the end effector of FIG. 3.

As shown best in FIGS. 3 and 4, end effector (50) includes a lower jaw (52) that supports a stapling assembly in the form of a replaceable staple cartridge (70), and an upper jaw

(54) that presents an anvil (56) having a plurality of staple forming pockets (58). Upper jaw (54) is configured to pivot relative to lower jaw (52) to clamp tissue between staple cartridge (70) and anvil (56) and subsequently form staples deployed by staple cartridge (70). End effector (50) further includes an elongate firing member (60) configured to translate distally through end effector (50) to drive staples from staple cartridge (70) toward anvil (56) and simultaneously cut tissue with a distally presented cutting edge (62). Accordingly, end effector (50) is operable to clamp, staple, and cut tissue.

As shown best in FIGS. 1 and 2, handle assembly (20) further includes a pistol grip (24), a closure trigger (26), and a firing trigger (28). Closure trigger (26) is pivotable toward pistol grip (24) to pivotably actuate upper jaw (54) toward lower jaw (52) and thereby close end effector (50) on tissue. Firing trigger (28) is then pivotable toward pistol grip (24) to fire end effector (50) on the clamped tissue. More specifically, actuation of firing trigger (28) causes firing member (60) to translate distally through end effector (50), including staple cartridge (70), to thereby staple and simultaneously cut the clamped tissue.

As shown in FIGS. 3-5B, staple cartridge (70) includes a cartridge body (72) having an upwardly facing deck (74), an elongate slot (76) extending along a central axis of cartridge body (72) and opening upwardly through deck (74), and a plurality of staple openings (78) (also known as apertures) extending through deck (74) on each side of elongate slot (76). Each staple opening (78) slidably houses an unformed staple (80) and a respective staple driver (82) positioned beneath staple (80). A lower tray (84), also known as a pan, encloses an underside of cartridge body (72) and thereby retains staples (80) and staple drivers (82) within cartridge body (72). A wedge sled (86) is slidably disposed within cartridge body (72) and includes upwardly presented cam surfaces configured to engage the undersides of staple drivers (82).

Figure 5A:
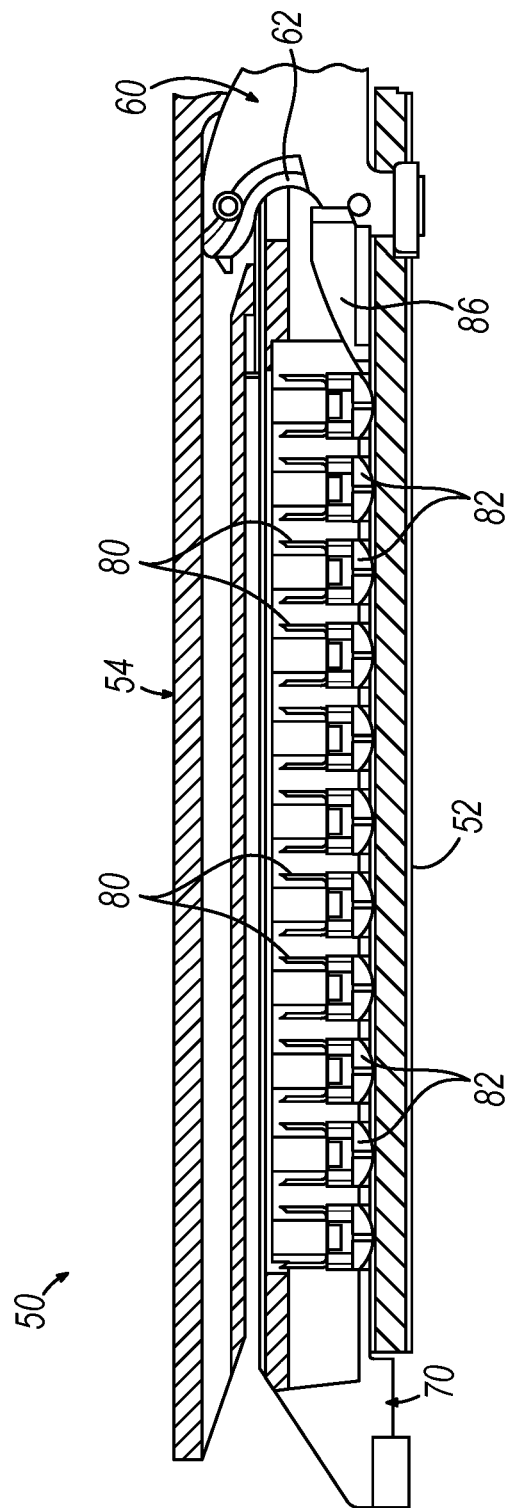
FIG. 5A depicts a side cross-sectional view of the end effector of FIG. 3, taken along line 5-5 of FIG. 3, with a firing member in a proximal position.
Figure 5B:
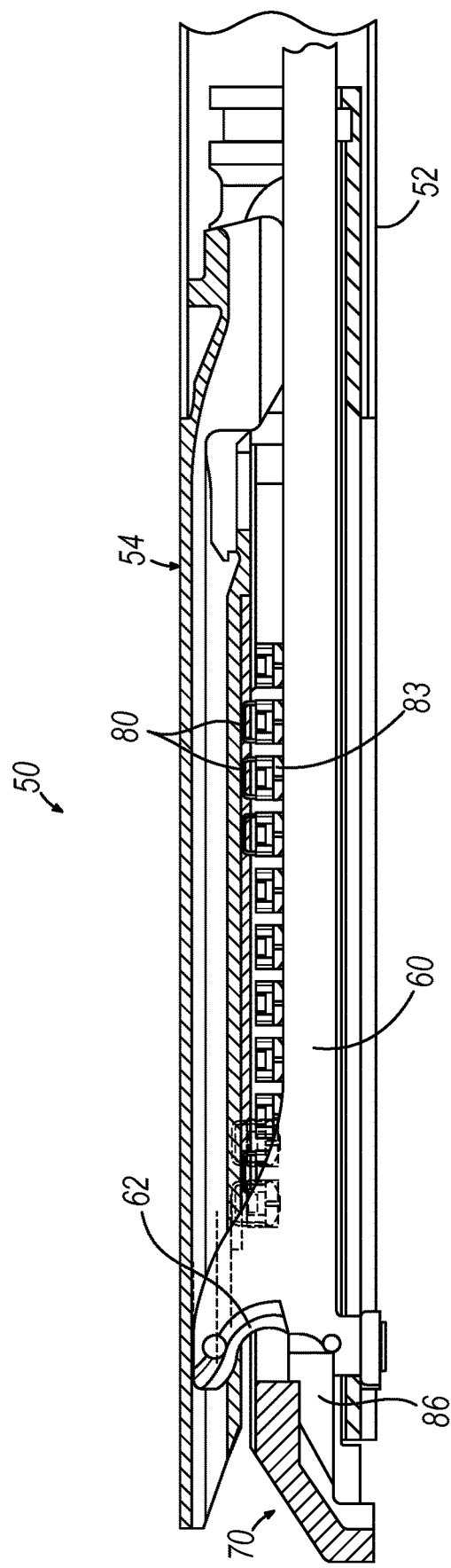
FIG. 5B depicts a side cross-sectional view of the end effector of FIG. 3, taken along line 5-5 of FIG. 3, with the firing member in a distal position.

FIGS. 5A-5B show a firing stroke of surgical stapler (10) during which firing member (60) is actuated distally through end effector (50), including elongate slot (76) of staple cartridge (70). A distal end of firing member (60) drives wedge sled (86) distally to cam staple drivers (82) upwardly and thereby drive the respective staples (80) outwardly from staple openings (78). The legs of staples (80) pass through clamped tissue (not shown) and are then formed by staple forming pockets (58) of anvil (56) (see FIG. 3). Simultaneously, the clamped tissue is severed by cutting edge (62) of firing member (60).

Figure 6:
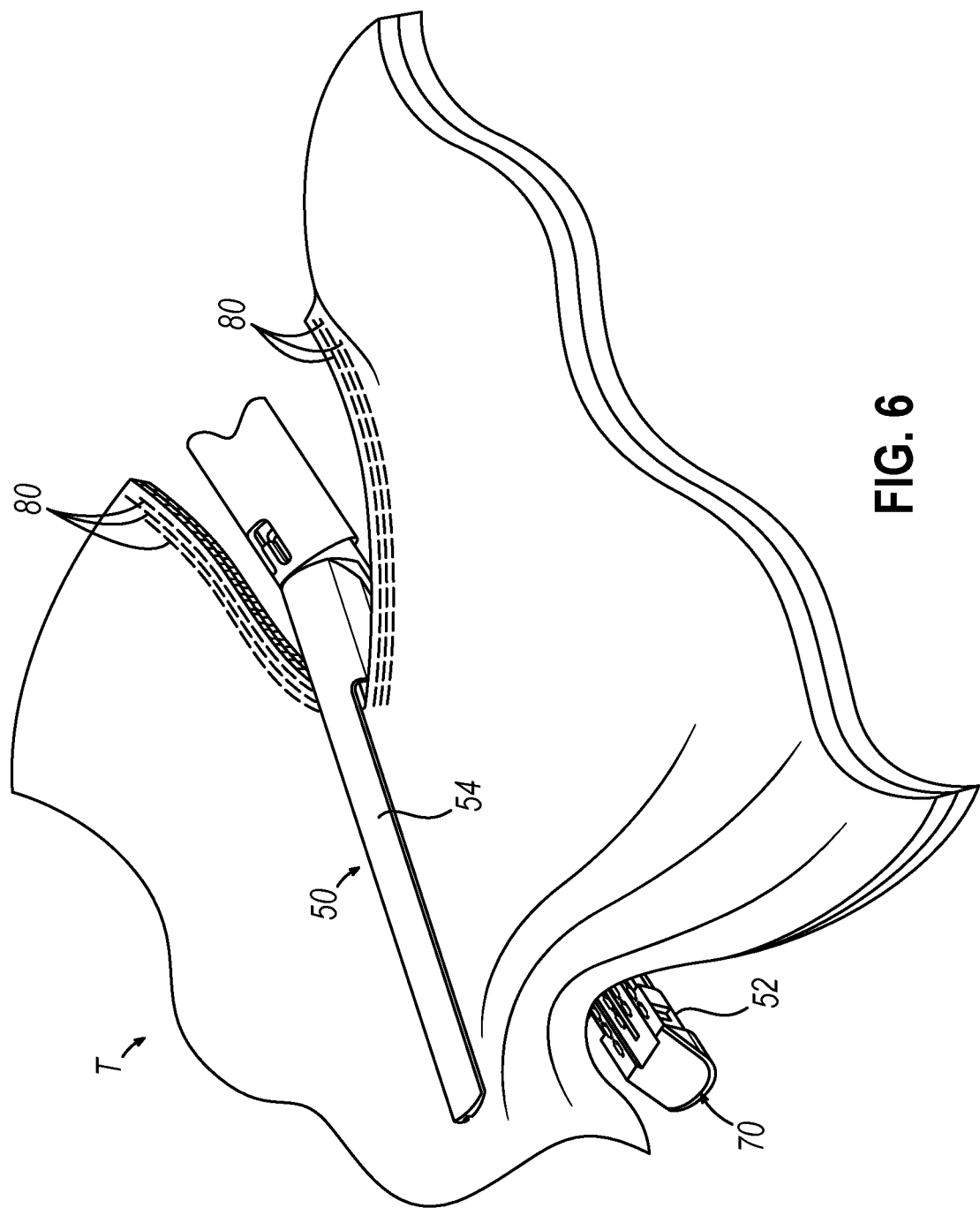
FIG. 6 depicts a perspective view of the end effector of FIG. 3, positioned at tissue and having been fired once in the tissue.

FIG. 6 shows end effector (50) after having been actuated through a single firing stroke through tissue (T). Cutting edge (62) of firing member (60) has cut through tissue (T), and staple drivers (82) have driven three alternating rows of staples (80) through tissue (T) on each side of the cut line produced by cutting edge (62). After the first firing stroke is completed, end effector (50) is withdrawn from the patient, spent staple cartridge (70) is replaced with a new staple cartridge (70), and end effector (50) is then again inserted into the patient to reach the stapling site for further cutting and stapling. This process may be repeated until the desired quantity and pattern of firing strokes across the tissue (T) has been completed.

Surgical stapler (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. EXEMPLARY BUTTRESS ASSEMBLY

In some instances, it may be desirable to equip end effector (50) of surgical stapler (10) with an adjunct, also known as a buttress or a tissue thickness compensator, to reinforce the mechanical fastening of tissue provided by staples (80). Such a buttress may prevent the applied staples (80) from pulling through the tissue and may otherwise reduce a risk of tissue tearing at or near the site of applied staples (80). In addition to or as an alternative to providing structural support and integrity to a line of staples (80), a buttress may provide various other kinds of effects such as spacing or gap-filling, administration of therapeutic agents, and/or other effects. In some instances, a buttress may be provided on upper deck (74) of staple cartridge (70). In some other instances, a buttress may be provided on the surface of anvil (56) that faces staple cartridge (70). It should also be understood that a first buttress may be provided on upper deck (74) of staple cartridge (70) while a second buttress is provided on anvil (56) of the same end effector (50).

A. Exemplary Composition of Buttress Assembly

Figure 7:
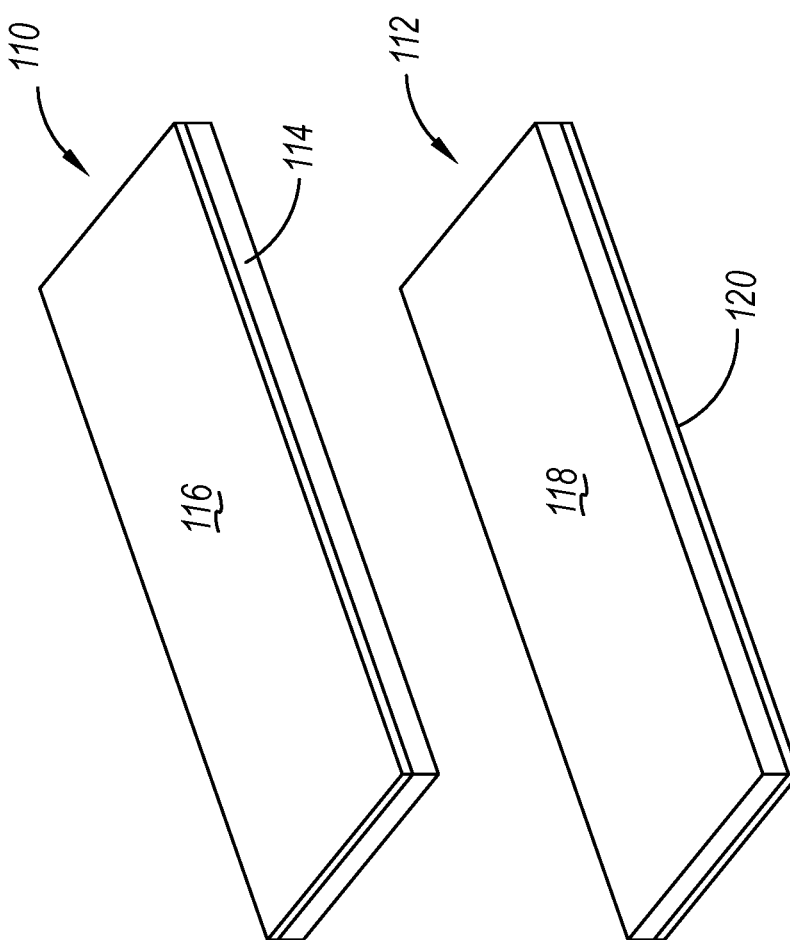
FIG. 7 depicts a perspective view of an exemplary pair of adjuncts in the form of buttress assemblies, each of which may be applied to a jaw of the end effector of FIG. 3.

FIG. 7 shows an exemplary pair of adjuncts in the form of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (80). By way of example only, each buttress body (114, 118) may comprise a mesh of polyglactin 910 material by Ethicon, Inc. of Somerville, New Jersey. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to an underside (124) of anvil (56). Similarly, adhesive layer (120) is provided on buttress body (118) to adhere buttress body (118) to upper deck (74) of staple cartridge (70). Such an adhesive material may provide proper positioning of buttress body (114, 118) before and during actuation of end effector (50); then allow buttress body (114, 118) to separate from end effector (50) after end effector (50) has been actuated, without causing damage to buttress body (114, 118) that is substantial enough to compromise the proper subsequent functioning of buttress body (114, 118).

B. Exemplary Stapling of Tissue with Buttress Assemblies

Figure 8C:
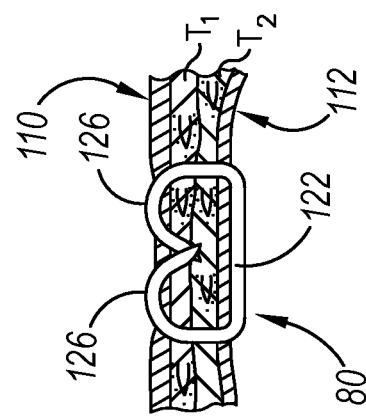
FIG. 8C depicts a cross-sectional view of a formed staple and the buttress assemblies of FIG. 8A after having been secured to the tissue by the end effector of FIG. 3.
Figure 8B:
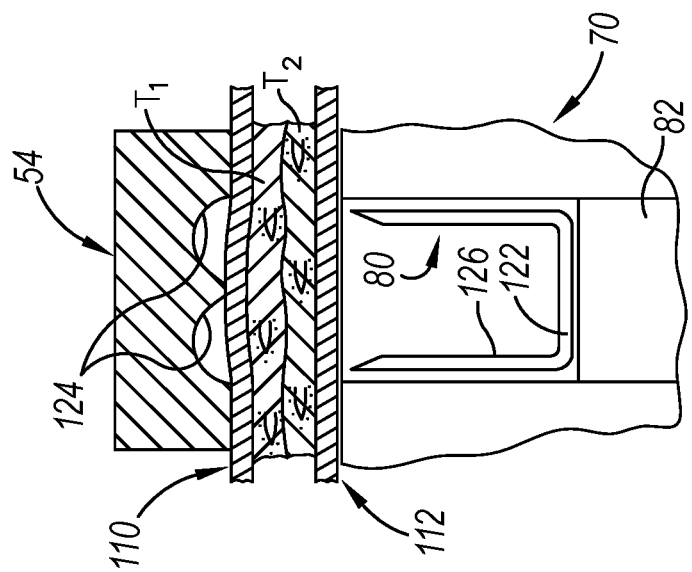
FIG. 8B depicts a cross-sectional end view of the end effector and buttress assemblies of FIG. 8A, showing the end effector jaws in a closed state on the tissue.
Figure 8A:
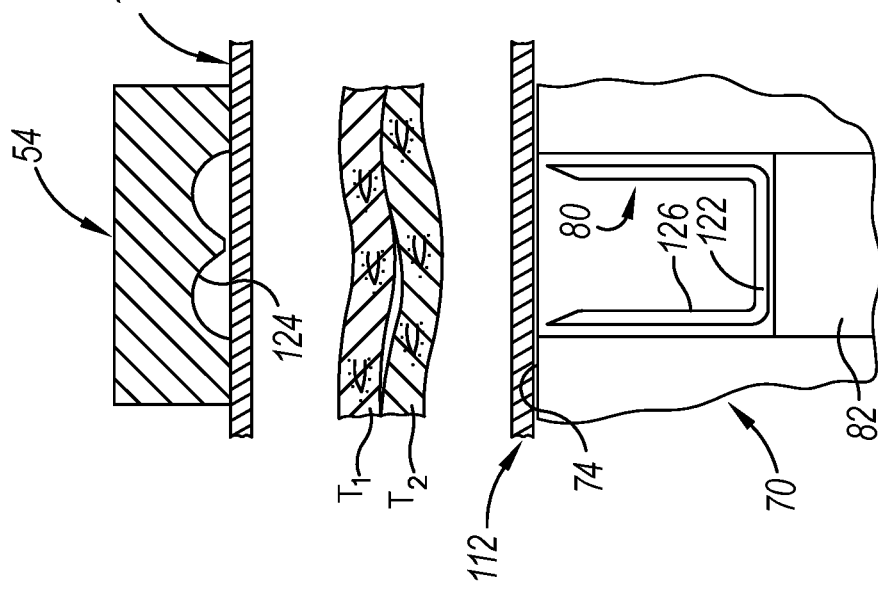
FIG. 8A depicts a cross-sectional end view of a portion of the end effector of FIG. 3 with the buttress assemblies of FIG. 7 applied to the upper and lower jaws of the end effector, showing the end effector jaws in an open state with tissue positioned between the upper and lower jaws.

FIGS. 8A-8C show an exemplary sequence in which surgical stapler end effector (50), which has been loaded with buttress assemblies (110, 112), is actuated to drive staples (80) through two opposed layers of tissue ($T_1$, $T_2$), with buttress assemblies (110, 112) being secured to the same layers of tissue ($T_1$, $T_2$) by staples (80). In particular, FIG. 8A shows layers of tissue ($T_1$, $T_2$) positioned between anvil (56) and staple cartridge (70), with anvil (56) in the open position. Buttress assembly (110) is adhered to underside (124) of anvil (56) via adhesive layer (116); while buttress assembly (112) is adhered to upper deck (74) of staple cartridge (70) via adhesive layer (120). Layers of tissue ($T_1$, $T_2$) are thus interposed between buttress assemblies (110, 112). Next, anvil (56) is closed against staple cartridge (70) such that layers of tissue ($T_1$, $T_2$) are compressed between anvil (56) and staple cartridge (70), with buttress assemblies (110, 112) engaging opposite surfaces of tissue layers ($T_1$, $T_2$). End effector (50) is then fired as described above, driving staple (80) through buttress assemblies (110, 112) and tissue ($T_1$, $T_2$). As shown in FIG. 8C, a crown (122) of driven staple (80) captures and retains buttress assembly (112) against layer of tissue ($T_2$). Deformed legs (126) of staple (80) capture and retain buttress assembly (110) against layer of tissue ($T_1$).

Figure 9:
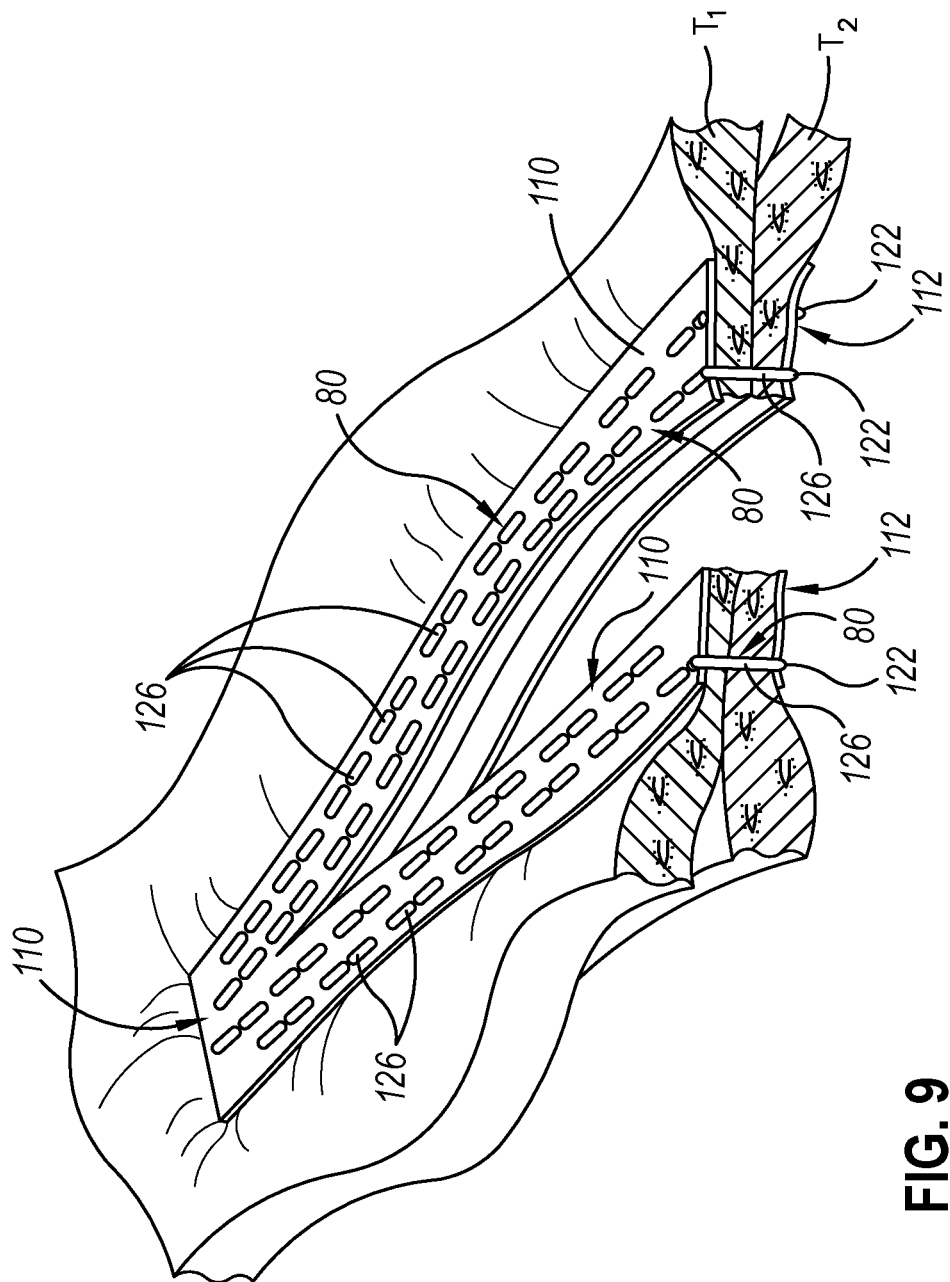
FIG. 9 depicts a perspective view of formed staples and the buttress assemblies of FIG. 8A after having been secured to the tissue by the end effector of FIG. 3.
Figure 10:
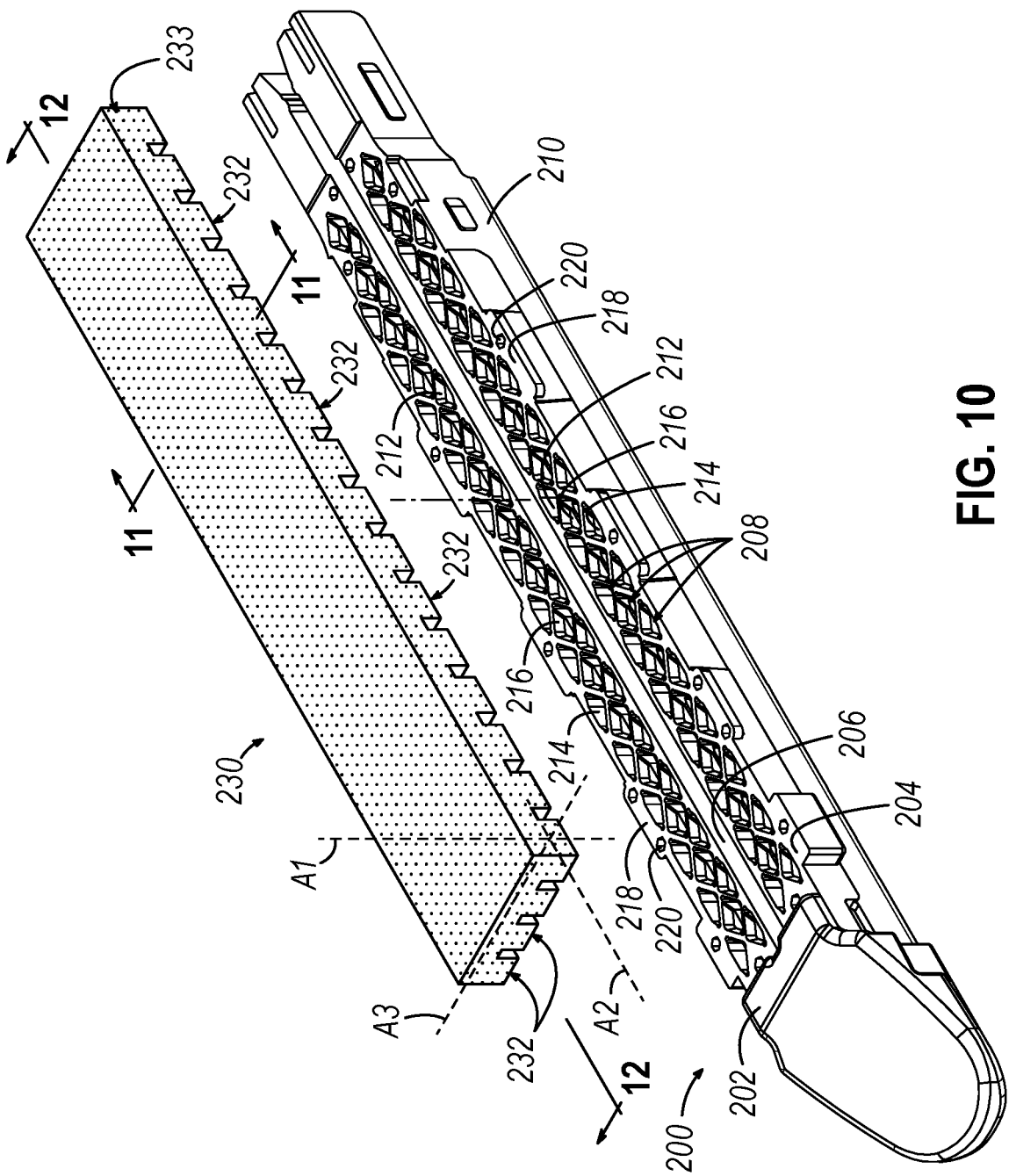
FIG. 10 depicts a perspective view of another exemplary staple cartridge in combination with a first alternative exemplary adjunct.

A series of staples (80) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (50) is pulled away from tissue ($T_1$, $T_2$) after deploying staples (80) and buttress assemblies (110, 112), buttress assemblies (110, 112) disengage end effector such that buttress assemblies (110, 112) remain secured to tissue ($T_1$, $T_2$) with staples (80). Buttress assemblies (110, 112) thus provide structural reinforcement to the lines of staples (80) formed in tissue ($T_1$, $T_2$). As can also be seen in FIG. 9, distally presented cutting edge (62) of firing member (60) also cuts through a centerline of buttress assemblies (110, 112), separating each buttress assembly (110, 112) into a corresponding pair of sections, such that each section remains secured to a respective severed region of tissue ($T_1$, $T_2$).

During use, surgical instrument (10) may be actuated multiple times during a single surgical procedure such that it may be desirable to enable an operator to repeatedly and easily load buttress assemblies (110, 112) onto lower jaw and anvil (16, 18) during that single surgical procedure. Accordingly, it may be desirable to use an adjunct applicator, also referred to as a buttress applier cartridge, to apply buttress assemblies (110, 112) to lower jaw and anvil (16, 18). Exemplary versions of such an applicator are disclosed in U.S. patent application Ser. No. 17/022,520, entitled "Method of Applying Buttress to End Effector of Surgical Stapler," filed Sep. 16, 2020, issued as U.S. Pat. No. 11,669,093 on May 30, 2023, the disclosure of which is incorporated by reference herein.

It will be appreciated that exemplary adjuncts and adjunct applicators may be further configured in accordance with one or more teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and U.S. Pat. Pub. No. 2012/0080336, entitled "Staple Cartridge Comprising Staples Positioned Within a Compressible Portion Thereof," published Apr. 5, 2012, now abandoned, the disclosures of which are incorporated by reference herein.

III. EXEMPLARY COMPRESSIBLE ADJUNCT

Figure 11:
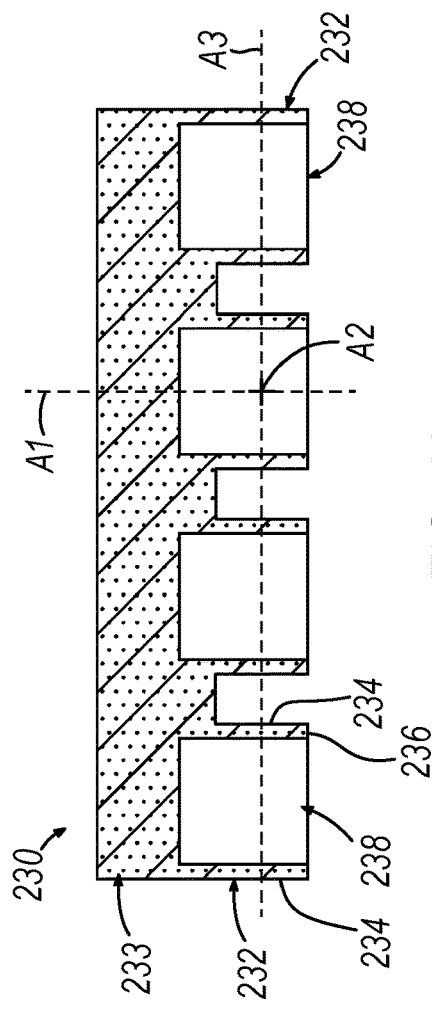
FIG. 11 depicts a cross-sectional view of the adjunct of FIG. 10, taken along line 11-11 of FIG. 10.
Figure 12:
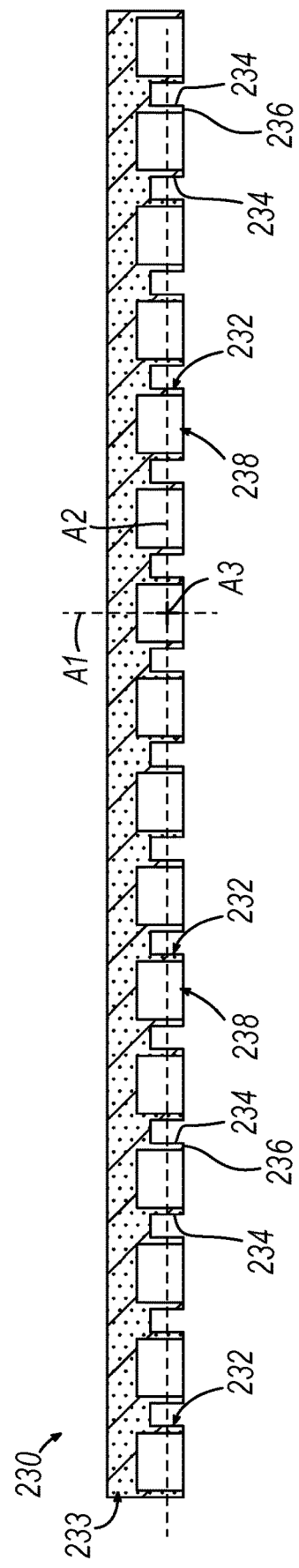
FIG. 12 depicts a cross-sectional view of the adjunct of FIG. 10, taken along line 12-12 of FIG. 10.

In some instances, it may be desirable to employ an adjunct having an enhanced degree of compressibility in a direction orthogonal to the stapling surfaces of end effector (50). Such an adjunct may be configured to apply a compression spring force to stapled tissue consistently along the entire length of the formed staple pattern, thereby ensuring a secure seal of tissue having a thickness that varies along a length of the formed staple pattern and end effector (50). FIGS. 10-12 show an example of such an adjunct (230), also referred to herein as a buttress or cushion, in combination with a staple cartridge (200). Staple cartridge (200) and adjunct (230) are configured for use with end effector (50) and are similar to staple cartridge (70) and buttress assembly (110, 112) described above except as otherwise described below.

It will be appreciated that staple cartridge (200) and/or adjunct (230) may be further configured in accordance with teachings of any one of more the following references, the disclosures of which are incorporated by reference herein: U.S. Pat. No. 10,441,285, entitled "Tissue Thickness Compensator Comprising Tissue Ingrowth Features," issued Oct. 15, 2019; U.S. Pat. No. 10,524,788, entitled "Compressible Adjunct with Attachment Regions," issued Jan. 7, 2020; U.S. Pat. No. 10,568,621, entitled "Surgical Staple Buttress with Integral Adhesive for Releasably Attaching to a Surgical Stapler," issued Feb. 25, 2020; U.S. Pat. No. 10,588,623, entitled "Adhesive Film Laminate," issued Mar. 17, 2020; U.S. Pat. No. 10,624,861, entitled "Tissue Thickness Compensator Configured to Redistribute Compressive Forces," issued Apr. 21, 2020; U.S. Pat. No. 10,667,808, entitled "Staple Cartridge Comprising an Absorbable Adjunct," issued Jun. 2, 2020; U.S. Pat. No. 10,945,731, entitled "Tissue Thickness Compensator Comprising Controlled Release and Expansion," issued Mar. 16, 2021; U.S. Pat. No. 10,966,722, entitled "Adjunct Materials and Methods of Using Same in Surgical Methods for Tissue Sealing," issued Apr. 6, 2021; U.S. Pat. No. 11,058,425, entitled "Implantable Layers for a Surgical Instrument," issued Jul. 13, 2021; and U.S. Pat. Pub. No. 2019/0200978, entitled "Tissue Ingrowth Materials and Method of Using the Same," published Jul. 4, 2019, issued as U.S. Pat. No. 11,219,451 on Jan. 11, 2022.

As shown in FIG. 10, staple cartridge (200) includes a cartridge body (202) having an upwardly facing deck (204), an elongate slot (206) extending along a central axis of cartridge body (202) and opening upwardly through deck (204), and a plurality of staple openings (208) extending through deck (204) on each side of elongate slot (206). Each staple opening (208) slidably houses an unformed staple (not shown), similar to staple (80), and a respective staple driver (not shown), similar to staple driver (82), configured to drive the staple outwardly toward anvil (56) to be formed. A lower tray (210) of staple cartridge (200) retains the staples and staple drivers within cartridge body (202).

Cartridge body (202) of the present example further includes a plurality of upwardly-opening recesses (212, 214, 216) formed in deck (204) and having base surfaces through which staple openings (208) extend. More specifically, on each side of elongate slot (206), deck (204) includes an inner row of triangular recesses (212) each having a medial apex that points transversely away from elongate slot (206); an outer row of triangular recesses (214) each having a medial apex that points transversely toward elongate slot (206); and a middle row of diamond-shaped recesses (216) each having an inner medial apex that points transversely toward elongate slot (206) and an opposed outer medial apex that points transversely away from elongate slot (206). Recesses (212, 214, 216) may cooperate to more securely grip and thereby stabilize clamped tissue during stapling and cutting of the clamped tissue.

Cartridge body (202) of the present example further includes a plurality of elongate tabs (218) projecting laterally outwardly from deck (204) on each lateral side of cartridge body (202). Tabs (218) of the present example are spaced apart from one another in a longitudinal direction, and each tab (218) has a generally rounded rectangular shape. Cartridge body (202) further includes a plurality of attachment openings (220) spaced apart from one longitudinally on each side of elongate slot (206), with each attachment opening (220) being smaller than a staple opening (208) and having a hexagonal shape. In the present version, each tab (218) includes at least one attachment opening (220). Attachment openings (220) may be configured to facilitate releasable attachment of an adjunct, such as adjunct (230), to staple cartridge deck (204).

Adjunct (230) has a plurality of sub-structures in the form of three-dimensional, resiliently compressible (or collapsible) nodules (232) that define a lower portion of adjunct (230) and are integrally connected with one another, via an upper portion (233) of adjunct (230), in a plurality of linear arrays defining a lattice structure having an elongate rectangular shape.

Each nodule (232) of the present example has a generally cuboid shape defining four side surfaces (234), a lower surface (236), and an opening (238) in lower surface (236) that extends along a vertical central axis (A1) of nodule (232) and defines an open, hollow interior of nodule (232). Additionally, each nodule (232) is symmetrical about its centroid along a second axis (A2) of nodule (232) that extends horizontally in a proximal-distal direction parallel to the length of adjunct (230), and along a third axis (A3) of nodule (232) that extends horizontally in a direction traverse to the length of adjunct (230), where each axis (A1, A2, A3) extends through the centroid.

Adjunct (230) may be formed of an elastic, bioabsorbable polymeric material having a suitable degree of elasticity that enables adjunct (230) to compress and resiliently resume its original shape. In the present example, each nodule (232) of adjunct (230) is resiliently compressible in such a manner along at least each of its three axes (A1, A2, A3).

IV. EXEMPLARY STAPLE LEG SUPPORT FEATURES

In some instances, it may be desirable to provide a stapling assembly, such as a staple cartridge, or an adjunct with one or more features for guiding the legs of staples (80) as the legs exit the respective staple openings during deployment of staples (80). For example, such guidance of the legs of staples (80) may promote vertical alignment of the legs of staples (80) with the corresponding staple forming pockets as the legs exit the respective staple openings, and thus inhibit longitudinal (e.g., distal) sweeping of the legs which may otherwise be caused by movement (e.g., "flow") of the tissue being stapled and which may result in improper staple formation. Exemplary versions of such staple leg support features are described in greater detail below. Unless otherwise described, it will be appreciated that such staple leg support features may be applied to a stapling assembly similar to staple cartridge (70) described above in connection with FIGS. 3-6, to a multi-layer adjunct similar to buttress assemblies (110, 112) described above in connection with FIGS. 7-9, or to a compressible monolithic adjunct similar to adjunct (230) described above in connection with FIGS. 10-12.

Figure 13:
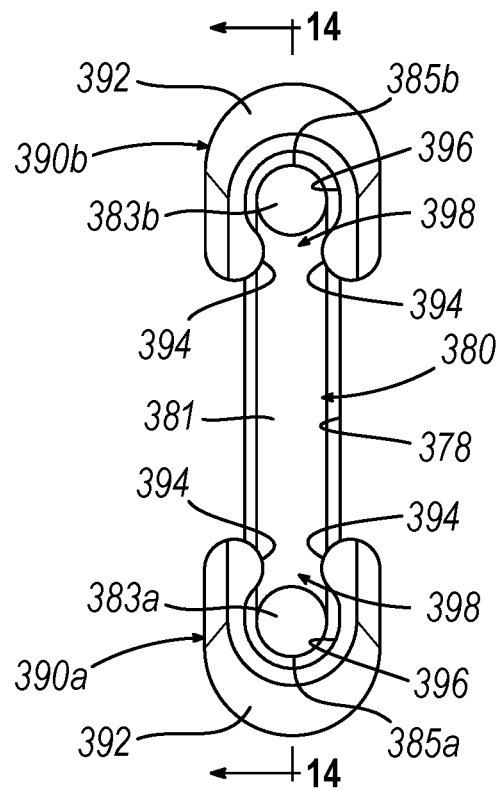
FIG. 13 depicts a top plan view of a portion of another exemplary staple cartridge for use with the end effector of FIG. 3 and having pocket extending members for guiding respective staple legs during deployment of staples out of staple openings of the staple cartridge.
Figure 14:
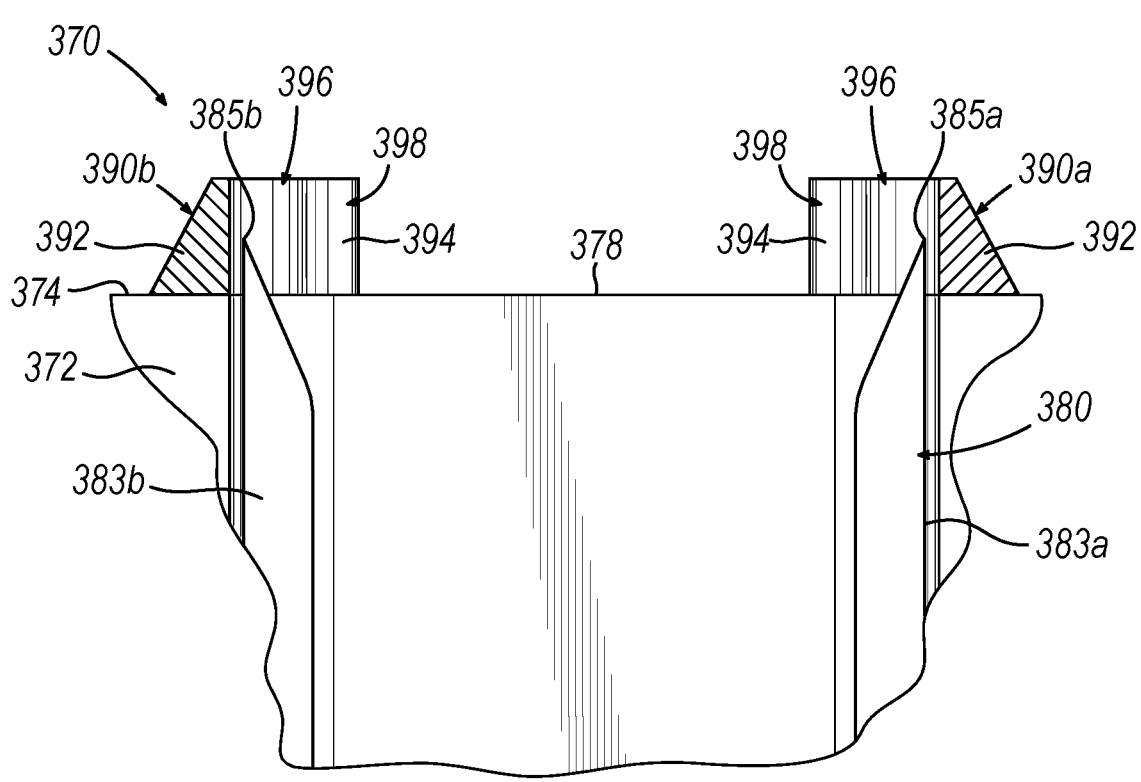
FIG. 14 depicts a cross-sectional view of the staple cartridge of FIG. 13, taken along line 14-14 of FIG. 13.

A. Exemplary Staple Cartridge with Pocket Extending Members for Guiding Staple Legs FIGS. 13-14 show a portion of another exemplary staple cartridge (370) configured to deploy staples (380) (one shown) toward corresponding staple forming pockets of an anvil (not shown), such as staple forming pockets (58) of anvil (56). Staple cartridge (370) is configured for use with end effector (50), and is similar to staple cartridge (70) described above except as otherwise described below. In this regard, staple cartridge (370) includes a cartridge body (372) having an upwardly facing deck (374), an elongate slot (not shown) similar to slot (76) extending along a central axis of cartridge body (372) and opening upwardly through deck (374), and a plurality of staple openings (378) (one shown) extending through deck (374) on each side of the elongate slot. Each staple opening (378) slidably houses an unformed staple (380) and a respective staple driver (not shown) similar to staple drivers (82) positioned beneath staple (380). A lower tray (not shown) similar to lower tray (84) encloses an underside of cartridge body (372) and thereby retains staples (380) and the staple drivers within cartridge body (372). A wedge sled (not shown) similar to wedge sled (86) is slidably disposed within cartridge body (372) and includes upwardly presented cam surfaces configured to engage the undersides of the staple drivers. Each staple (380) includes an elongate crown (381) and proximal and distal legs (383a, 383b) extending upwardly and generally perpendicularly from respective ends of crown (381) to respective sharp tips (385a, 385b).

Staple cartridge (370) of the present example further includes a plurality of staple leg constraints in the form of pocket extending members (390a, 390b) coupled to and extending upwardly from deck (374) at or near proximal and distal ends of each staple opening (378). More particularly, staple cartridge (370) includes a plurality of proximal pocket extending members (390a) (one shown) extending upwardly from deck (374) at or near proximal ends of corresponding staple openings (378), and a plurality of distal pocket extending members (390b) (one shown) extending upwardly from deck (374) at or near distal ends of corresponding staple openings (378), such that each staple opening (378) is longitudinally flanked by a corresponding pair of proximal and distal pocket extending members (390a, 390b).

Each pocket extending member (390a, 390b) includes a generally U-shaped body (392) having a pair of laterally-opposed detents (394) extending laterally toward each other. In the example shown, U-shaped body (392) of each pocket extending member (390a, 390b) defines a staple leg receptacle (396) for receiving a corresponding leg (383a, 383b) of the staple (380) slidably housed within the respective staple opening (378), and detents (394) are spaced apart from each other to define an expandable constriction (398) at a longitudinally-inner end of the corresponding staple leg receptacle (396). More particularly, detents (394) of each proximal pocket extending member (390a) are spaced apart from each other to define the respective expandable constriction (398) at a distal end of the corresponding staple leg receptacle (396), and detents (394) of each distal pocket extending member (390b) are spaced apart from each other to define the respective expandable constriction (398) at a proximal end of the corresponding staple leg receptacle (396).

As best shown in FIG. 13, each staple leg receptacle (396) is sized and configured to slidably receive the corresponding leg (383a, 383b) for vertically guiding the corresponding leg (383a, 383b) out of the respective staple opening (378) toward the corresponding staple forming pockets (58) as staples (380) are driven outwardly from staple openings (378) by the staple drivers. For example, each staple leg receptacle (396) may have a partially circular cross-sectional shape and may have a cross dimension (e.g., diameter) slightly greater than a diameter of the corresponding leg (383a, 383b). In this manner, each leg (383a, 383b) may be capable of sliding vertically through the corresponding staple leg receptacle (396) while being laterally and/or longitudinally constrained thereby. More particularly, each proximal leg (383a) may be laterally and proximally constrained by the corresponding staple leg receptacle (396) such that both lateral and proximal movement of each proximal leg (383a) may be resisted by the corresponding staple leg receptacle (396). Likewise, each distal leg (383b) may be laterally and distally constrained by the corresponding staple leg receptacle (396) such that both lateral and distal movement of each distal leg (383b) may be resisted by the corresponding staple leg receptacle (396).

Each expandable constriction (398) is sized and configured to inhibit longitudinal passage of the corresponding leg (383a, 383b) therethrough for maintaining the corresponding leg (383a, 383b) within the respective staple leg receptacle (396) as staples (380) are driven outwardly from staple openings (378) by the staple drivers. For example, each expandable constriction (398) may have an unexpanded cross dimension (e.g., width) substantially less than the diameter of the corresponding leg (383a, 383b). In this manner, each leg (383a, 383b) may be inhibited from longitudinally exiting the corresponding staple leg receptacle through the corresponding expandable constriction (398) and thus may be longitudinally constrained thereby. More particularly, each proximal leg (383a) may be distally constrained by the corresponding expandable constriction (398) such that distal movement of each proximal leg (383a) may be resisted by the corresponding expandable constriction (398). Likewise, each distal leg (383b) may be proximally constrained by the corresponding expandable constriction (398) such that proximal movement of each distal leg (383b) may be resisted by the corresponding expandable constriction (398). Thus, each leg (383a, 383b) may be collectively constrained both laterally and longitudinally by the corresponding staple leg receptacle (396) and expandable constriction (398).

In some versions, each expandable constriction (398) may be configured to be laterally expanded by the crown (381) of the respective staple (380) to permit vertical passage of the corresponding crown (381) therethrough, such as during loading of staples (380) into staple openings (378) from above deck (374), as staples (380) are driven outwardly from staple openings (378) by the staple drivers, and/or after staples (380) are driven outwardly from staple openings (378) by the staple drivers. For example, detents (394) may be configured to be urged laterally away from each other when engaged by the corresponding crown (381) as the corresponding crown (381) is being pushed downwardly toward the respective staple opening (378) and/or as the corresponding crown (381) is being driven upwardly out of the respective staple opening (378) to transition the respective expandable constriction (398) to an expanded state in which the respective expandable constriction (398) has an expanded cross dimension (e.g., width) substantially equal to or slightly greater than a diameter of the corresponding crown (381). In this manner, each crown (381) may be capable of passing vertically through each of the corresponding expandable constrictions (398) for loading staples (380) into staple cartridge (370) and/or releasing staples (380) from staple cartridge (370).

In this regard, bodies (392) may each be constructed of a soft and/or flexible (e.g., resilient) material, such as an elastic and/or polymeric material having a suitable degree of flexibility that enables lateral expansion of expandable constrictions (398) by the corresponding crowns (381), while having a suitable degree of stiffness for resisting longitudinal passage of legs (383a, 383b) through expandable constrictions (398). In some versions, such a material may have a suitable degree of elasticity that enables each expandable constriction (398) to be expanded by the corresponding crown (381) and resiliently resume its original shape. In addition, or alternatively, such a material may have a suitable degree of elasticity that enables each body (392) to compress (e.g., vertically) when tissue is clamped against deck (374) and resiliently resume its original shape. In such cases, staple leg receptacles (396) and expandable constrictions (398) may continue to function as set forth above while body (392) is compressed. In other words, the compression of body (392) may not interfere with the ability of staple leg receptacles (396) and expandable constrictions (398) to constrain legs (383a, 383b) laterally and longitudinally. In the example shown, bodies (392) each flare outwardly from the tops thereof toward deck (374) to provide added stiffness to the respective pocket extending members (390a, 390b). In any event, bodies (392) may each be coupled to cartridge body (372) in any suitable manner, such as via overmolding bodies (392) onto deck (374) of cartridge body (372).

In some versions, pocket extending members (390a, 390b) may enable deck (374) of staple cartridge (370) to be positioned at a relatively low height, at least by comparison to decks of staple cartridges lacking pocket extending members (390a, 390b), such as deck (74) of staple cartridge (70). For example, pocket extending members (390a, 390b) may protect tips (385a, 385b) of staples (380) within the corresponding staple leg receptacles (396) as shown in FIG. 14, such that deck (374) may be positioned at a relatively low height below tips (385a, 385b) of staples (380) without causing a snag hazard between tips (385a, 385b) and tissue. In some cases, such a relatively low height of deck (374) may enable funneling of tissue clamped against deck (374) toward the elongate slot of staple cartridge (370) for severing, such as by cutting edge (62) of firing member (60). In addition, or alternatively, the wedge sled of staple cartridge (370) may include a sharp or blunt fin member for lifting tissue above deck (374) toward an optimal cutting plane, as described in greater detail below. It will also be appreciated that pocket extending members (390a, 390b) may enhance gripping of tissue by staple cartridge (370).

B. Exemplary Suture Strands for Guiding Staple Legs

Figure 15:
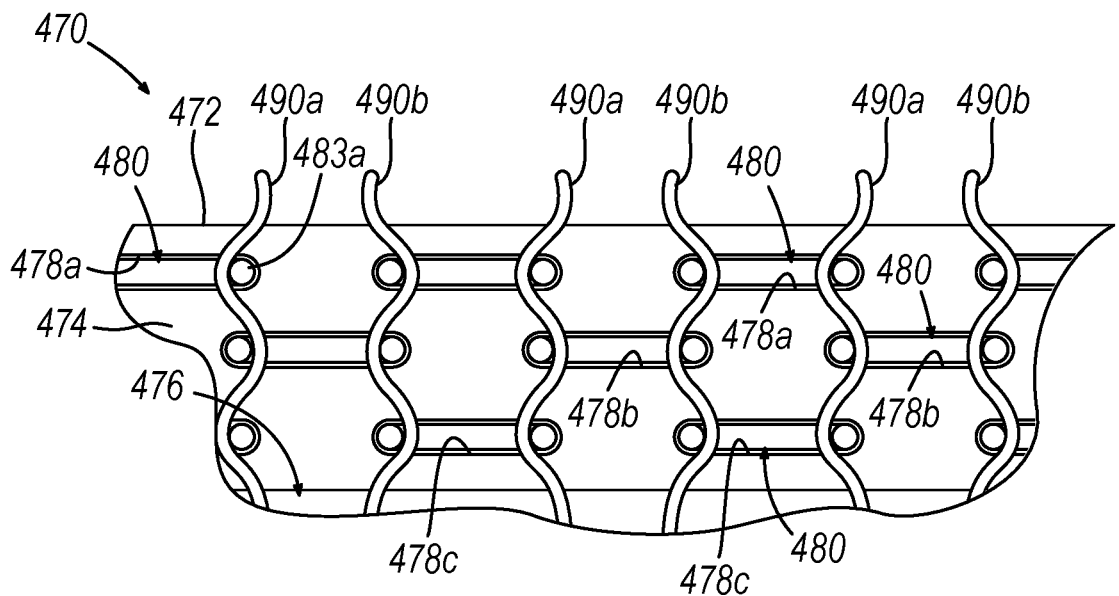
FIG. 15 depicts a top plan view of a portion of another exemplary staple cartridge for use with the end effector of FIG. 3, showing a plurality of suture strands strung laterally across a deck of the staple cartridge over staple openings of the staple cartridge for guiding respective staple legs during deployment of staples out of the staple openings.
Figure 16:
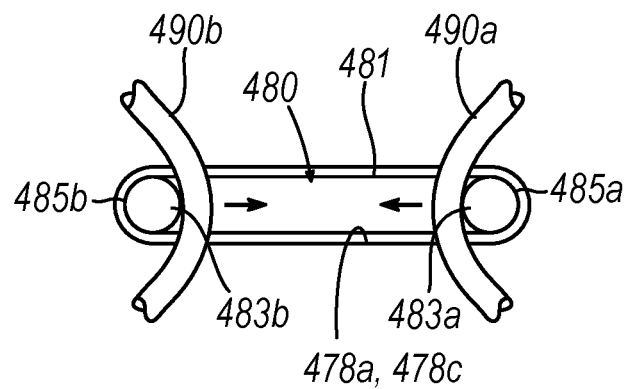
FIG. 16 depicts a top plan view of one of the staple openings of the staple cartridge of FIG. 15, showing the corresponding suture strands resisting longitudinally-inner movement of the respective staple legs toward each other.

FIGS. 15-16 show a portion of another exemplary staple cartridge (470) configured to deploy staples (480) toward corresponding staple forming pockets of an anvil (not shown), such as staple forming pockets (58) of anvil (56). Staple cartridge (470) is configured for use with end effector (50), and is similar to staple cartridge (70) described above except as otherwise described below. In this regard, staple cartridge (470) includes a cartridge body (472) having an upwardly facing deck (474), an elongate slot (476) extending along a central axis of cartridge body (472) and opening upwardly through deck (474), and a plurality of staple openings (478a, 478b, 478c) extending through deck (474) on each side of elongate slot (476). Each staple opening (478a, 478b, 478c) slidably houses an unformed staple (480) and a respective staple driver (not shown) similar to staple drivers (82) positioned beneath staples (480). A lower tray (not shown) similar to lower tray (84) encloses an underside of cartridge body (472) and thereby retains staples (480) and the staple drivers within cartridge body (472). A wedge sled (not shown) similar to wedge sled (86) is slidably disposed within cartridge body (472) and includes upwardly presented cam surfaces configured to engage the undersides of the staple drivers. Each staple (480) includes an elongate crown (481) and proximal and distal legs (483a, 483b) extending upwardly and generally perpendicularly from respective ends of crown (481) to respective sharp tips (485a, 485b).

In the example shown, a plurality of staple leg constraints in the form of suture strands (490a, 490b) are strung laterally across deck (474) over staple openings (478a, 478b, 478c) near longitudinal ends thereof. More particularly, a plurality of first suture strands (490a) are strung laterally across deck (474) over a corresponding laterally-outer staple opening (478a) near a proximal end thereof, over a corresponding laterally-intermediate staple opening (478b) near a distal end thereof, and over a corresponding laterally-inner staple opening (478c) near a proximal end thereof. Similarly, a plurality of second suture strands (490b) are strung laterally across deck (474) over a corresponding laterally-outer staple opening (478a) near a distal end thereof, over a corresponding laterally-intermediate staple opening (478b) near a proximal end thereof, and over a corresponding laterally-inner staple opening (478c) near a distal end thereof. In this manner, each staple opening (478a, 478b, 478c) is partially positioned under a corresponding pair of first and second suture strands (490a, 490b) near proximal and distal ends of the staple opening (478a, 478b, 478c). In the example shown, laterally-intermediate staple openings (478b) are each offset in the longitudinal direction from the laterally-adjacent outer and inner staple openings (478a, 478c), such that each suture strand (490a, 490b) is routed along a generally serpentine path over the corresponding staple openings (478a, 478b, 478c). In some versions, suture strands (490a, 490b) may be coupled to each other. For example, suture strands (490a, 490b) may be defined by respective portions of a single elongate suture (not shown). In any event, each suture strand (490a, 490b) may be taut to inhibit longitudinal and/or lateral movement of suture strands (490a, 490b) relative to deck (474).

As shown, each suture strand (490a, 490b) is longitudinally spaced apart from the corresponding longitudinal end of each respective staple opening (478a, 478b, 478c) for capturing a corresponding leg (483a, 483b) of the staple (480) slidably housed within each respective staple opening (478a, 478b, 478c) between the suture strand (490a, 490b) and the corresponding longitudinal end. More particularly, each suture strand (490a, 490b) is longitudinally spaced apart from the corresponding longitudinal end of each respective staple opening (478a, 478b, 478c) for vertically guiding the corresponding legs (483a, 483b) out of the respective staple openings (478a, 478b, 478c) toward the corresponding staple forming pockets (58) as staples (480) are driven outwardly from staple openings (478a, 478b, 478c) by the staple drivers. For example, each first suture strand (490a) may be distally spaced apart from the proximal end of the corresponding laterally-outer staple opening (478a) by a distance slightly greater than a diameter of the corresponding proximal leg (483a), proximally spaced apart from the distal end of the corresponding laterally-intermediate staple opening (478b) by a distance slightly greater than a diameter of the corresponding distal leg (483b), and distally spaced apart from the proximal end of the corresponding laterally-inner staple opening (478c) by a distance slightly greater than a diameter of the corresponding proximal leg (483a). Similarly, each second suture strand (490b) may be proximally spaced apart from the distal end of the corresponding laterally-outer staple opening (478a) by a distance slightly greater than a diameter of the corresponding distal leg (483b), distally spaced apart from the proximal end of the corresponding laterally-intermediate staple opening (478b) by a distance slightly greater than a diameter of the corresponding proximal leg (483a), and proximally spaced apart from the distal end of the corresponding laterally-inner staple opening (478c) by a distance slightly greater than a diameter of the corresponding distal leg (483b).

In this manner, each leg (483a, 483b) may be capable of sliding vertically between the corresponding suture strand (490a, 490b) and the corresponding longitudinal end of the respective staple opening (478a, 478b, 478c) while being laterally and/or longitudinally constrained thereby. More particularly, each laterally-inner and laterally-outer proximal leg (483a) may be distally constrained by the corresponding first suture strand (490a) via the tension therein, such that distal movement of each such proximal leg (483a) may be resisted by the corresponding first suture strand (490a). Likewise, each laterally-intermediate distal leg (483b) may be proximally constrained by the corresponding first suture strand (490a) via the tension therein, such that proximal movement of each such distal leg (483b) may be resisted by the corresponding first suture strand (490a). Each laterally-inner and laterally-outer distal leg (483b) may be proximally constrained by the corresponding second suture strand (490b) via the tension therein, such that proximal movement of each such distal leg (483b) may be resisted by the corresponding second suture strand (490b). Likewise, each laterally-intermediate proximal leg (483a) may be distally constrained by the corresponding second suture strand (490b) via the tension therein, such that distal movement of each such proximal leg (483a) may be resisted by the corresponding second suture strand (490b).

In some versions, each suture strand (490a, 490b) may be configured to be released from deck (474) and deployed with the corresponding staples (480) after guiding the corresponding legs (483a, 483b) out of the respective staple openings (478a, 478b, 478c) in the manner described above. For example, each suture strand (490a, 490b) may be configured to be driven upwardly away from deck (474) when engaged by the corresponding crowns (481) as the corresponding crowns (481) are being driven upwardly out of the respective staple openings (478a, 478b, 478c). In this regard, suture strands (490a, 490b) may each be constructed of any suitable bioabsorbable materials having a suitable degree of strength to hold sufficient tension for constraining legs (483a, 483b) of staples (480) in the manner described above, including but not limited to PDS (polydioxanone), polyglactin 910, or polyglecaprone 25. In some versions, suture strands (490a, 490b) may each be woven into a multi-layer adjunct similar to buttress assemblies (110, 112) described above in connection with FIGS. 7-9, or woven into a compressible monolithic adjunct similar to adjunct (230) described above in connection with FIGS. 10-12. In such cases, suture strands (490a, 490b) may be releasably attached to deck (474) by virtue of the releasable attachment of the adjunct to deck (474), and may likewise be deployed together with the adjunct. In other versions, staple cartridge (470) may include various gripping members (not shown) extending upwardly from deck (474) around staple openings (478a, 478b, 478c) to enhance gripping of tissue by staple cartridge (470), and suture strands (490a, 490b) may be wound around or otherwise anchored to such gripping members for releasably attaching suture strands (490a, 490b) to deck (474).

C. Exemplary Adjunct with Bores for Guiding Staple Legs

FIGS. 17-20 show another exemplary compressible adjunct (530) configured for releasable attachment to a staple cartridge (500). Staple cartridge (500) and adjunct (530) are configured for use with end effector (50) and are similar to staple cartridge (200) and adjunct (230) described above except as otherwise described below. In this regard, staple cartridge (500) includes a cartridge body (502) having an upwardly facing deck (504), an elongate slot (506) extending along a central axis of cartridge body (502) and opening upwardly through deck (504), and a plurality of staple openings (508) extending through deck (504) on each side of elongate slot (506). Each staple opening (508) slidably houses an unformed staple (580), and a respective staple driver (not shown), similar to staple driver (82), configured to drive the corresponding staple (580) outwardly toward anvil (56) to be formed. A lower tray (not shown) of staple cartridge (500) retains staples (580) and the staple drivers within cartridge body (502). Cartridge body (502) of the present example further includes a plurality of upwardly-opening recesses (512, 514) formed in deck (504) and having base surfaces through which staple openings (508) extend. More specifically, on each side of elongate slot (506), deck (504) includes an inner row of triangular recesses (512) each having a medial apex that points transversely away from elongate slot (506); an outer row of triangular recesses (514) each having a medial apex that points transversely toward elongate slot (506); and a middle row of diamond-shaped recesses (not shown) each having an inner medial apex that points transversely toward elongate slot (506) and an opposed outer medial apex that points transversely away from elongate slot (506). Each staple (580) includes an elongate crown (581) and a pair of legs (583) extending upwardly and generally perpendicularly from respective ends of crown (581) to respective sharp tips (585).

Adjunct (530) of the present example has a plurality of three-dimensional, resiliently compressible nodules (532) that are integrally connected with one another in a plurality of linear arrays defining a lattice structure having an elongate rectangular shape. In the present example, adjunct (530) includes two lateral adjunct sections (530a, 530b) configured for placement on respective sides of staple cartridge slot (506), each including inner and outer axial rows of nodules (532) each extending in a proximal-distal direction, and a plurality of transverse rows of nodules (532) each extending in a direction transverse to a length of staple cartridge (500). In the example shown, each lateral adjunct section (530a, 530b) also includes a medial axial row of nodules (532) extending in the proximal-distal direction and offset from each of the inner and outer axial rows of nodules (532) in the proximal-distal direction. Additionally, adjunct (530) of the present example has a height of only one nodule (532). It will be appreciated that adjunct (530) of other versions may have various other quantities and configurations of nodules (532). In the example shown, lateral adjunct sections (530a, 530b) are coupled to each other by a plurality of lateral webs (533) extending therebetween and disposed at discrete locations along a length of adjunct (530). Lateral webs (533) may be configured to be severed by cutting edge (62) of firing member (60) during translation thereof through the staple cartridge slot to separate lateral adjunct sections (530a, 530b) from each other.

Each compressible nodule (532) of adjunct (530) is symmetrical about a pair of planes (not shown) that extend through a centroid of nodule (532), including: a first vertical plane that extends parallel to the sidewalls of staple cartridge slot (506); and a second vertical plane that extends transversely to the length of staple cartridge slot (506). Each nodule (532) of the present example has a hollow interior and includes a generally rectangular cuboid central body (534), a tapered lower trunk (536a) projecting downwardly from central body (534), and four tapered side trunks (536b) opposed from each other relative to the first and second vertical planes to define the symmetrical geometrical configuration described above. Each trunk (536a, 536b) has a generally elliptical cross-section. In the example shown, each nodule (532) lacks an upper trunk opposite lower truck (536a) along its vertical axis, such that a generally rectangular aperture (538) is defined by the upper end of each central body (534) at a tissue-engaging face of adjunct (530). Adjunct (530) of the present example also includes a plurality of vertically-extending notches (539) (FIG. 19) defined by corresponding laterally-adjacent pairs of side trunks (536), the purposes of which are described below.

In the example shown, adjunct (530) further includes a plurality of attachment features in the form of tabs (540). Tabs (540) extend generally downwardly from the lower trunk (536a) of a respective nodule (532) and include a generally vertically-extending gripping surface (542). More particularly, the tab (540) of each inner nodule (532) extends downwardly from a laterally-inner portion of the respective lower trunk (536a) and includes a laterally-inwardly facing gripping surface (542), while the tab (540) of each outer nodule (532) extends generally downwardly from a laterally-outer portion of the respective lower trunk (536a) and includes a laterally-outwardly facing gripping surface (542), the purposes of which are described below.

As shown, each inner and outer nodule (532) is interconnected with one or two laterally-adjacent medial nodule(s) (532), via side trunks (536b). Each medial nodule (532) is interconnected with one or two laterally-adjacent inner nodule(s) (532) and with one or two laterally-adjacent outer nodule(s) (532), via side trunks (536b). In the example shown, some of the inner nodules (532) of one lateral adjunct section (530a) are coupled to laterally-adjacent inner nodules (532) of the other lateral adjunct section (530b) by lateral webs (533).

Figure 20:
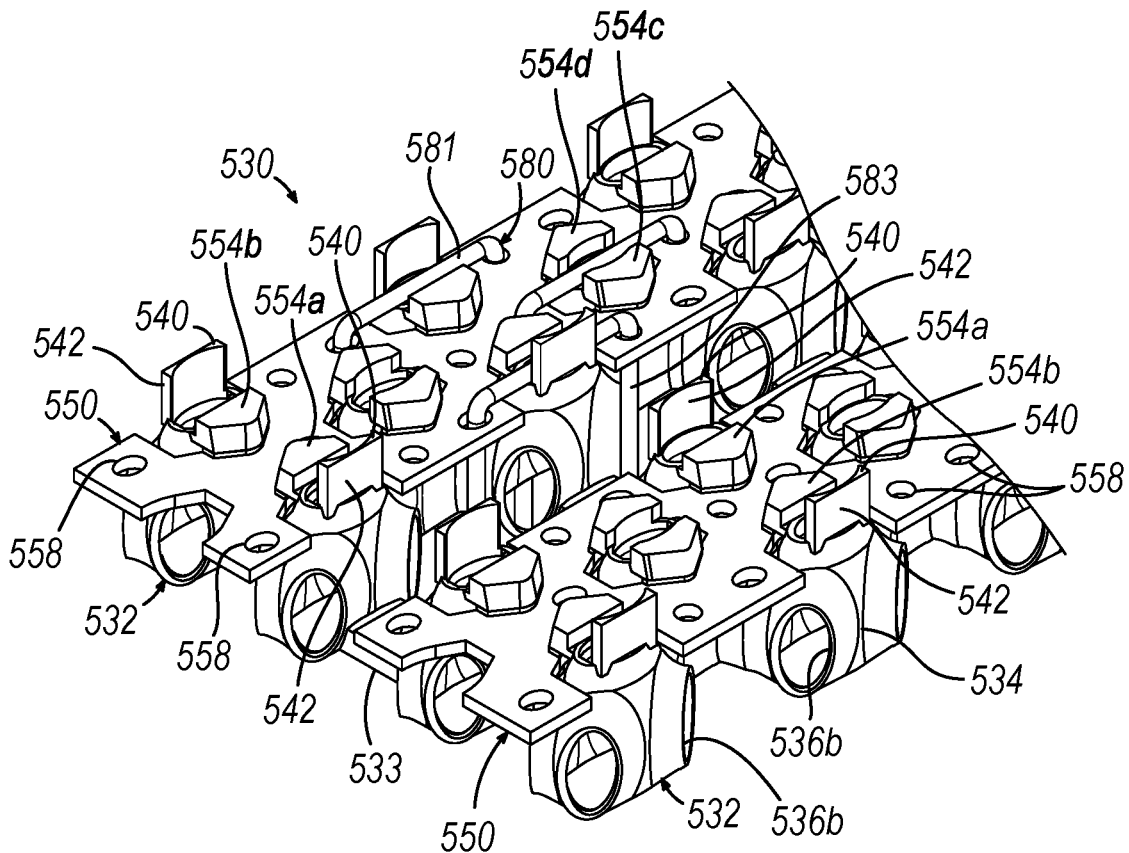
FIG. 20 depicts a bottom perspective view of the adjunct of FIG. 17.

Each lateral adjunct section (530a, 530b) of the present example also includes a base (550) interconnecting lower portions of the respective nodules (532) with each other. More particularly, each nodule (532) is coupled to the respective base (550) along a portion of the corresponding lower trunk (536a). In this regard, each base (550) includes an upper web (552) and a plurality of generally pyramid-shaped lower protrusions (554a, 554b, 554c, 554d) extending downwardly from upper web (552). As best shown in FIG. 20, each base (550) includes inner and outer axial rows of protrusions (554a, 554b) each extending in a proximal-distal direction, and further includes medial-inner and medial-outer axial rows of protrusions (554c, 554d) each extending in the proximal-distal direction and offset from each of the inner and outer axial rows of protrusions (554a, 554b) in the proximal-distal direction. Each inner protrusion (554a) has a generally triangular cross-section with a medial apex that points transversely away from elongate slot (506), and each outer protrusion (554b) has a generally triangular cross-section with a medial apex that points transversely toward elongate slot (506). Each medial-inner protrusion (554c) has a generally triangular cross-section with a medial apex that points transversely toward elongate slot (506), and each medial-outer protrusion (554d) has a generally triangular cross-section with a medial apex that points transversely away from elongate slot (506), such that each laterally-adjacent pair of medial-inner and medial-outer protrusions (554c, 554d) collectively have a bifurcated, generally diamond-shaped cross-section with an inner medial apex that points transversely toward elongate slot (506) and an opposed outer medial apex that points transversely away from elongate slot (506).

In the example shown, a portion of each protrusion (554a, 554b, 554c, 554d) extends laterally from web (552) to a portion of the lower trunk (536a) of a corresponding nodule (532) to thereby serve as a bridge between web (552) and the corresponding nodule (532). More particularly, a portion of each inner protrusion (554a) extends laterally inwardly from web (552) to a laterally outer side of the lower trunk (536a) of a corresponding inner nodule (532), and a portion of each outer protrusion (554b) extends laterally outwardly from web (552) to a laterally inner side of the lower trunk (536a) of a corresponding outer nodule (532. A portion of each medial-inner protrusion (554c) extends laterally outwardly from web (552) to a laterally inner side of the lower trunk (536a) of a corresponding medial nodule (532), and a portion of each medial-outer protrusion (554d) extends laterally inwardly from web (552) to a laterally outer side of the lower trunk (536a) of a corresponding medial nodule (532), such that each medial nodule (532) may be coupled to web (552) on both lateral sides of the medial nodule (532) via a corresponding laterally-adjacent pair of medial-inner and medial-outer protrusions (554c, 554d).

Web (552) of the present example is spaced apart from each nodule (532) by a corresponding gap (556), and is only coupled to nodules (532) via the corresponding protrusion(s) (554a, 554b, 554c, 554d) to avoid interfering with the ability of nodules (532) to resiliently compress. In this regard, the interconnection of nodules (532) with each other via base (550) may improve pressure distribution across each respective lateral adjunct section (530a, 530b), while the spacing apart of nodules (532) from web (552) by gaps (556) (and/or the only partial coupling of each nodule (532) to web (552) via the corresponding protrusion(s) (554a, 554b, 554c, 554d)) may enable each nodule (532) to have a substantially same pressure profile as the respective nodule (532) would otherwise have in the absence of base (550).

Figure 18:
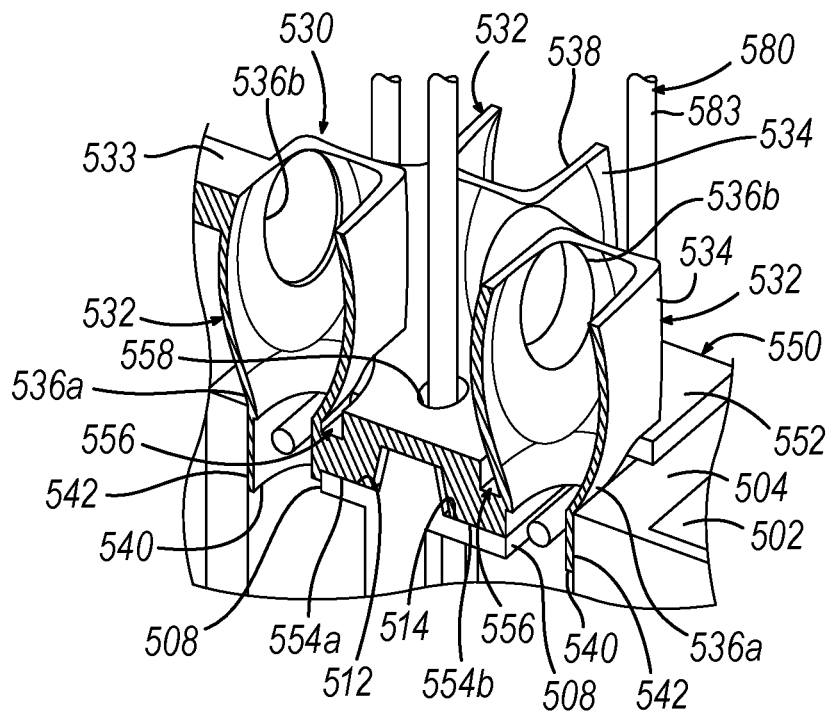
FIG. 18 depicts an enlarged cross-sectional end view of the staple cartridge and adjunct of FIG. 17, showing an upper web of the base coupled to lower trunks of the nodules via corresponding lower protrusions.
Figure 19:
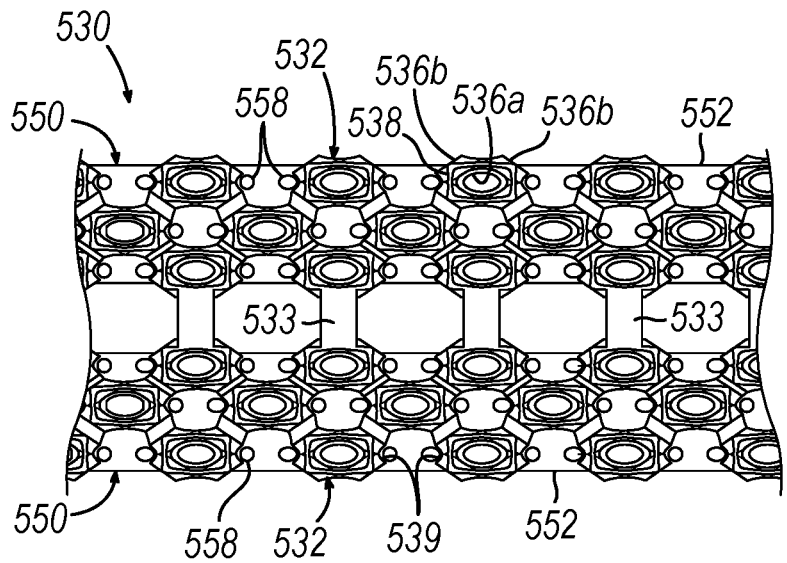
FIG. 19 depicts a top plan view of a portion of the adjunct of FIG. 17.

Each base (550) of the present example further includes a plurality of staple leg constraints in the form of bores (558) extending through the respective web (552) for receiving a leg (583) of a corresponding staple (580). As best shown in FIG. 18, each bore (558) is sized and configured to slidably receive the corresponding leg (583) for vertically guiding the corresponding leg (583) out of the respective staple opening (508) toward the corresponding staple forming pocket (58) as staples (580) are driven outwardly from staple openings (508) by the staple drivers. For example, each bore (558) may have a generally circular cross-sectional shape and may have a cross dimension (e.g., diameter) slightly greater than a diameter of the corresponding leg (583). In this manner, each leg (583) may be capable of sliding vertically through the corresponding bore (558) while being laterally and/or longitudinally constrained thereby. More particularly, each leg (583) may be laterally, proximally, and distally constrained by the corresponding bore (558) such that lateral, proximal, and distal movement of each leg (583) may be resisted by the corresponding bore (558). In the example shown, legs (583) of staples (580) may be further vertically guided along notches (539), which may resist lateral and/or longitudinal movement of each corresponding leg (583).

In this regard, adjunct (530) may be formed of an elastic, bioabsorbable polymeric (e.g., elastomeric) material having a suitable degree of elasticity that enables adjunct (530) to compress and resiliently resume its original shape, while having a suitable degree of stiffness for resisting stretching or other deformation of bores (558) by legs (583) as staples (580) are driven outwardly from staple openings (508) by the staple drivers. In the present example, each nodule (532) of adjunct (530) is resiliently compressible in such a manner along at least each of its three axes (e.g., its vertical axis along which lower trunk (536a) extends and its two horizontal axes along which respective pairs of side trunks (536b) extend). Additionally, adjunct (530) may be formed as a monolithic structure via an additive manufacturing process, for example. In this regard, any one or more of nodules (532), lateral webs (533), and/or base (550) may be integrally formed together as a unitary piece, such as via 3D-printing.

As best shown in FIG. 18, each nodule (532) of adjunct (530) is configured to overlie a corresponding recess (512, 514) and/or a corresponding staple opening (508) of staple cartridge (500) to enable the legs (583) of each staple (580) slidably housed within the respective staple opening (508) to pass vertically through the corresponding bores (558) during deployment of staples (580). In some versions, the tips (585) of each staple (580) are configured to protrude upwardly out of the corresponding staple openings (508) at least slightly above deck (504) and into the corresponding bores (558) prior to deployment of staples (580) to assist with retaining adjunct (530) on deck (504) and/or to protect tips (585) within the corresponding bores (558).

In some versions, at least a portion of the lower trunk (536a) of each nodule (532) may be received within the corresponding recess (512, 514) and/or staple opening (508) to promote such overlying of nodules (532) relative to the corresponding recesses (512, 514) and/or staple openings (508). In the example shown, tabs (540) of nodules (532) are at least partially received within the corresponding recess (512, 514) and/or staple opening (508) such that the respective gripping surface (542) frictionally engages a respective side surface of the corresponding recess (512, 514) and/or staple opening (508) to promote such overlying of nodules (532) relative to the corresponding recesses (512, 514) and/or staple openings (508). Protrusions (554a, 554b, 554c, 554d) of the present example are also at least partially received within corresponding recesses (512, 514) to promote such overlying of nodules (532) relative to the corresponding recesses (512, 514) and/or staple openings (508). More particularly, each inner protrusion (554a) is at least partially received within a corresponding inner recess (512), each outer protrusion (554b) is at least partially received within a corresponding outer recess (514), and each laterally-adjacent pair of medial-inner and medial-outer protrusions (554*c*, 554*d*) are collectively at least partially received within a corresponding medial recess.

Figure 17:
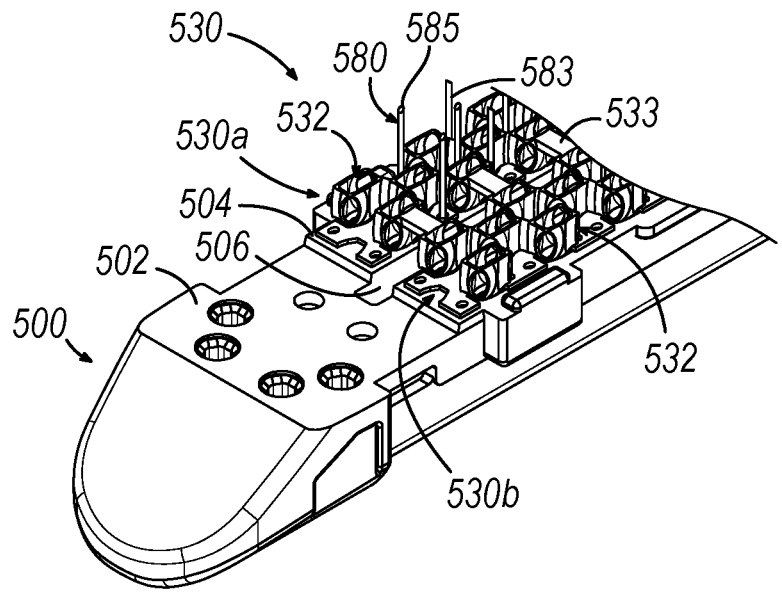
FIG. 17 depicts a perspective view of a portion of another exemplary staple cartridge in combination with another exemplary adjunct that has nodules configured to be flanked by the respective staple legs of staples deployed from the staple cartridge, and that further has a base with bores for guiding respective staple legs during deployment of the staples.

In any event, such overlying of nodules (532) relative to the corresponding recesses (512, 514) and/or staple openings (508) may also enable the legs (583) of each staple (580) slidably housed within the respective staple opening (508) to flank the corresponding nodule (532) during deployment of staples (580), as shown in FIG. 17. In this manner, the deformed legs (583) of each staple (580) capture and compress the corresponding nodule (532) against the crown (581) thereof when staples (580) are formed by staple forming pockets (58) of anvil (56). Such flanking of nodules (532) by the legs (583) of the corresponding staples (580) may also enable at least some staples (580) to avoid piercing the corresponding nodules (532) during deployment of staples (580). In some versions, adjunct (530) may be configured to provide a stress plateau when compressed for optimally compressing the stapled tissue over a predefined range of tissue thicknesses.

D. Exemplary Adjunct with Notches for Receiving Staple Crowns

FIGS. 21A-22B show another exemplary compressible adjunct (630) configured for releasable attachment to a staple cartridge (600). Staple cartridge (600) and adjunct (630) are configured for use with end effector (50) and are similar to staple cartridge (200) and adjunct (230) described above except as otherwise described below. In this regard, staple cartridge (600) includes a cartridge body (602) having an upwardly facing deck (604), an elongate slot (606) extending along a central axis of cartridge body (602) and opening upwardly through deck (604), and a plurality of staple openings (608) extending through deck (604) on each side of elongate slot (606). Each staple opening (608) slidably houses an unformed staple (680), and portion of a respective staple driver assembly (682) configured to drive the corresponding staple (680) outwardly toward anvil (56) to be formed. A lower tray (not shown) of staple cartridge (600) retains staples (680) and staple driver assemblies (682) within cartridge body (602). Cartridge body (602) of the present example further includes a plurality of upwardly-opening recesses (612, 616) formed in deck (604) and having base surfaces through which staple openings (608) extend. More specifically, on each side of elongate slot (606), deck (604) includes an inner row of triangular recesses (612) each having a medial apex that points transversely away from elongate slot (606); an outer row of triangular recesses (not shown) each having a medial apex that points transversely toward elongate slot (606); and a middle row of diamond-shaped recesses (616) each having an inner medial apex that points transversely toward elongate slot (606) and an opposed outer medial apex that points transversely away from elongate slot (606). Each staple (680) includes an elongate crown (681) and a pair of legs (683) extending upwardly and generally perpendicularly from respective ends of crown (681) to respective sharp tips (685).

Adjunct (630) of the present example has a plurality of three-dimensional, resiliently compressible polygonal (e.g., hexagonal) upper protrusions (632) extending upwardly from a planar base in the form of a web (633) having an elongate rectangular shape such that protrusions (632) are integrally connected with one another in a plurality of linear arrays defining a honeycomb structure atop web (633). In some versions, adjunct (630) may include two lateral adjunct sections (not shown) configured for placement on respective sides of staple cartridge slot (606), each including inner and outer axial rows of protrusions (632) each extending in a proximal-distal direction, and a medial axial row of protrusions (632) extending in the proximal-distal direction and offset from each of the inner and outer axial rows of protrusions (632) in the proximal-distal direction. Each protrusion (632) of the present example has a hollow interior and includes a pair of laterally-extending end walls (635*a*) and at least four obliquely-extending and/or longitudinally-extending sidewalls (635*b*) arranged to collectively define an open upper end (638) of the respective protrusion (632) at a tissue-engaging face of adjunct (630). In the example shown, each inner protrusion (632) is bifurcated by staple cartridge slot (606). For example, one half of each inner protrusion (632) may be incorporated into a first lateral adjunct section on a first side of staple cartridge slot (606), while the other half of each inner protrusion (632) may be incorporated into a second lateral adjunct section on a second side of staple cartridge slot (606). In some versions, walls (635*a*, 635*b*) may have a substantially uniform height relative to a top surface of web (633). For example, each wall (635*a*, 635*b*) may have a height of about 0.040 inch relative to the top surface of web (633).

As shown, each inner and outer protrusion (632) is interconnected with one or two laterally-adjacent medial protrusion(s) (632), via the respective walls (635) directly interfacing with each other. Each medial protrusion (632) is interconnected with one or two laterally-adjacent inner protrusion(s) (632) and with one or two laterally-adjacent outer protrusion(s) (632), via the respective walls (635) directly interfacing with each other.

Figure 22A:
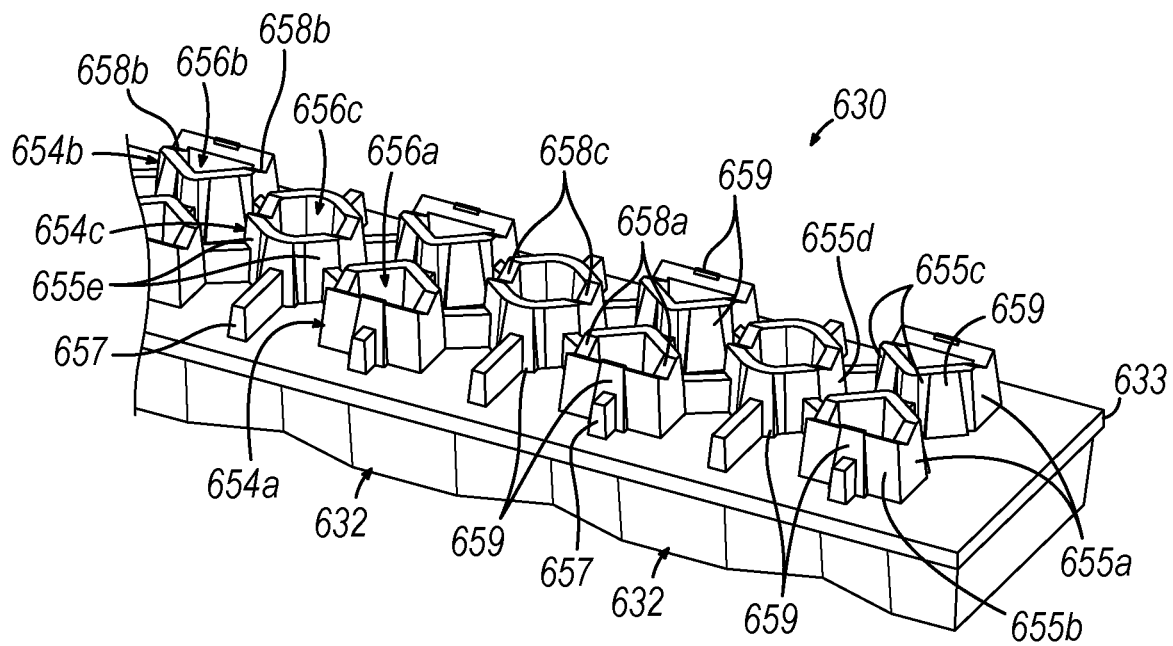
FIG. 22A depicts a bottom perspective view of the adjunct of FIG. 21A, showing the notches of the pyramid-shaped protrusions vacant prior to deployment of the staples.
Figure 22B:
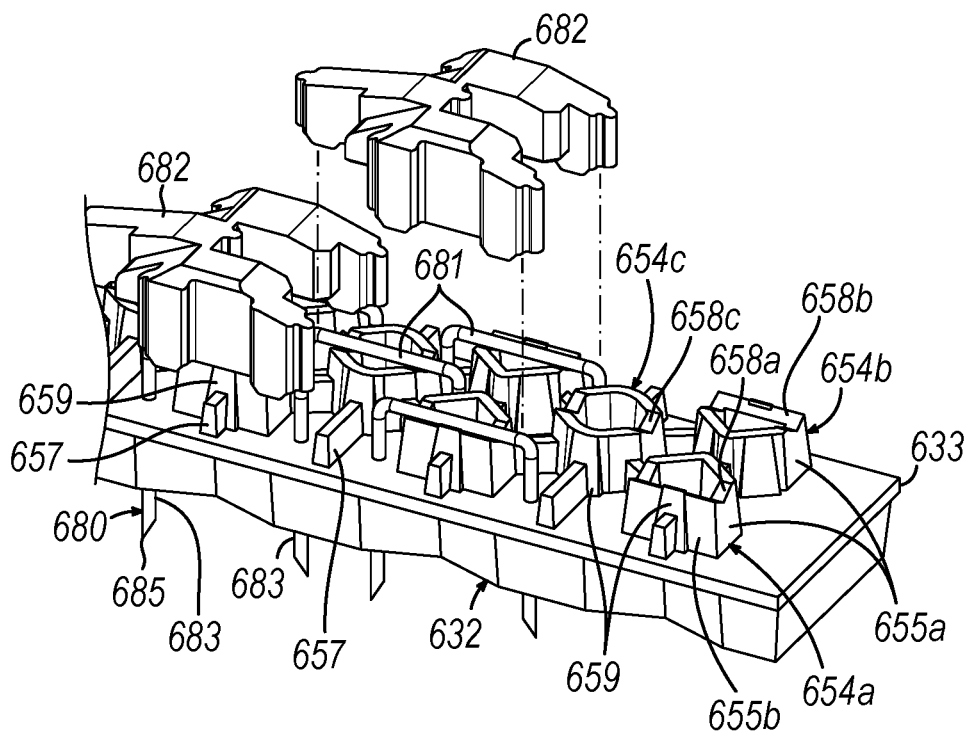
FIG. 22B depicts a bottom perspective view of the adjunct of FIG. 21A, showing the crowns of the staples engaged with the corresponding notches of the pyramid-shaped protrusions during deployment of the staples.

Adjunct (630) of the present example also has a plurality of staple leg constraints in the form of three-dimensional, resiliently compressible pyramid-shaped lower protrusions (654*a*, 654*b*, 654*c*) extending downwardly from web (633). As best shown in FIGS. 22A-22B, adjunct (630) includes inner and outer axial rows of protrusions (654*a*, 654*b*) each extending in a proximal-distal direction, and further includes a medial axial row of protrusions (654*c*) extending in the proximal-distal direction and offset from each of the inner and outer axial rows of protrusions (654*a*, 654*b*) in the proximal-distal direction. Each inner and outer protrusion (654*a*, 654*b*) of the present example has a hollow interior and includes a pair of laterally-extending end walls (655*a*), a longitudinally-extending sidewall (655*b*), and a pair of obliquely-extending sidewalls (655*c*) arranged to collectively define an open lower end (656*a*, 656*b*) of the respective protrusion (654*a*, 654*b*) at a stapler-engaging face of adjunct (630). More specifically, each inner protrusion (654*a*) has a generally pentagonal cross-section with a medial apex that points transversely away from elongate slot (606), and each outer protrusion (654*b*) has a generally pentagonal cross-section with a medial apex that points transversely toward elongate slot (606). Each medial protrusion (654*c*) of the present example has a hollow interior and includes a pair of laterally-extending end walls (655*d*) and four obliquely-extending sidewalls (655*e*) arranged to collectively define an open lower end (656*c*) of the respective protrusion (654*c*) at the stapler-engaging face of adjunct (630). More specifically, each medial protrusion (654*c*) has a generally hexagonal cross-section with an inner medial apex that points transversely toward elongate slot (606) and an opposed outer medial apex that points transversely away from elongate slot (606). In some versions, walls (655*a*, 655*b*, 655*c*, 655*d*, 655*e*) may have a substantially uniform height relative to a bottom surface of web (633). For example, each wall (655*a*, 655*b*, 655*c*, 655*d*, 655*e*) may have a height of about 0.039 inch relative to the bottom surface of web (633). Adjunct (630) also includes a plurality of stiffening ribs (657) extending outwardly from and/or between various protrusions (654a, 654b, 654c). In the example shown, locking ramps (659) extend along laterally-outer surfaces of protrusions (654a, 654b, 654c), the purposes of which are described below.

Each protrusion (654a, 654b, 654c) of the present example further includes a corresponding pair of longitudinally-aligned notches (658a, 658b, 658c) extending upwardly from the lower end thereof for receiving a crown (681) of a corresponding staple (680). More particularly, each inner protrusion (654a) includes a corresponding pair of longitudinally-aligned inner notches (658a) extending upwardly from lower ends of the respective end walls (655a). Likewise, each outer protrusion (654b) includes a corresponding pair of longitudinally-aligned outer notches (658b) extending upwardly from lower ends of the respective end walls (655a). Similarly, each medial protrusion (654c) includes a corresponding pair of longitudinally-aligned medial notches (658c) extending upwardly from lower ends of the respective end walls (655d).

As best shown in FIGS. 22A-22B, each pair of longitudinally-aligned notches (658a, 658b, 658c) is sized and configured to receive the corresponding crown (681) for seating or otherwise retaining the crown (681) against the respective protrusion (654a, 654b, 654c). For example, each notch (658a, 658b, 658c) may be generally V-shaped and may have a cross dimension (e.g., width) slightly greater than a diameter of the corresponding crown (681). In this manner, each crown (681) may be capable of engaging the corresponding notch (658a, 658b, 658c) while being laterally constrained thereby. More particularly, each crown (681) may be laterally constrained by the corresponding notches (658a, 658b, 658c) such that lateral movement of each crown (681) may be resisted by the corresponding notches (658a, 658b, 658c). In some versions, each leg (683) may be longitudinally constrained by the corresponding end walls (655a, 655d) which may resist longitudinally-inner movement of legs (683) toward each other.

In this regard, adjunct (630) may be formed of an elastic, bioabsorbable polymeric (e.g., elastomeric) material having a suitable degree of elasticity that enables adjunct (630) to compress and resiliently resume its original shape, while having a suitable degree of stiffness for resisting stretching or other deformation of notches (658a, 658b, 658c) by crowns (681) as staples (680) are driven outwardly from staple openings (608) by staple driver assemblies (682). In the present example, each protrusion (632, 654a, 654b, 654c) of adjunct (630) is resiliently compressible in such a manner in at least the proximal-distal, transverse, and vertical directions. Additionally, adjunct (630) may be formed as a unitary (e.g., monolithic) structure via an injection molding process, for example.

In this regard, open upper ends (638) of protrusions (632) are devoid of any undercuts (e.g., internal undercuts, occluded undercuts, etc.) or other geometrical features extending over the hollow interior of the respective protrusion (632) such that each hollow interior opens uninterruptedly to the respective open upper end (638) (e.g., without constricting inwardly). Likewise, open lower ends (656a, 656b, 656c) of protrusions (654a, 654b, 654c) are devoid of any undercuts (e.g., internal undercuts, occluded undercuts, etc.) or other geometrical features extending under the hollow interior of the respective protrusion (654a, 654b, 654c) such that each hollow interior opens uninterruptedly to the respective open lower end (656a, 656b, 656c) (e.g., without constricting inwardly).

It will be appreciated that the absence of undercuts or other geometrical features extending over the hollow interiors of protrusions (632) at upper ends (638) and/or the absence of undercuts or other geometrical features extending under the hollow interiors of protrusions (654a, 654b, 654c) at lower ends (656a, 656b, 656c) may enable injection molding of adjunct (630), since the presence of such undercuts or other geometrical features might otherwise interfere with the ability of two mold halves to be separated (e.g., opened) after injection molding adjunct (630) therein. More particularly, a first mold half (not shown) may include a first cavity configured to receive molten material for producing the upper features of adjunct (630) (e.g., at/above web (633)) while a second mold half (not shown) may include a second cavity configured to receive molten material for producing the lower features of adjunct (630) (e.g., at/below web (633)). Due to the absence of undercuts or other geometrical features extending over the hollow interiors of protrusions (632) at upper ends (638) and/or under the hollow interiors of protrusions (654a, 654b, 654c) at lower ends (656a, 656b, 656c), such first and second mold halves may be readily separated from each other (e.g., along a horizontal parting line) after injection molding adjunct (630) therein without disrupting the structural integrity of adjunct (630) or of either mold half.

As shown, the walls (635a, 635b) of each protrusion (632) taper outwardly from the respective upper end (638) toward (e.g., to) web (633) at one or more corresponding positive draft angles (e.g., relative to a vertical plane perpendicular to the horizontal parting line of the mold halves) for assisting with separation of the mold halves after injection molding adjunct (630) therein. Likewise, the walls (655a, 655b, 655c, 655d, 655e) of each protrusion (654a, 654b, 654c) taper outwardly from the respective lower end (656a, 656b, 656c) toward (e.g., to) web (633) at one or more corresponding positive draft angles (e.g., relative to a vertical plane perpendicular to the horizontal parting line of the mold halves) for assisting with separation of the mold halves after injection molding adjunct (630) therein. Stiffening ribs (657) and/or locking ramps (659) may be similarly tapered at positive draft angles.

Figure 21A:
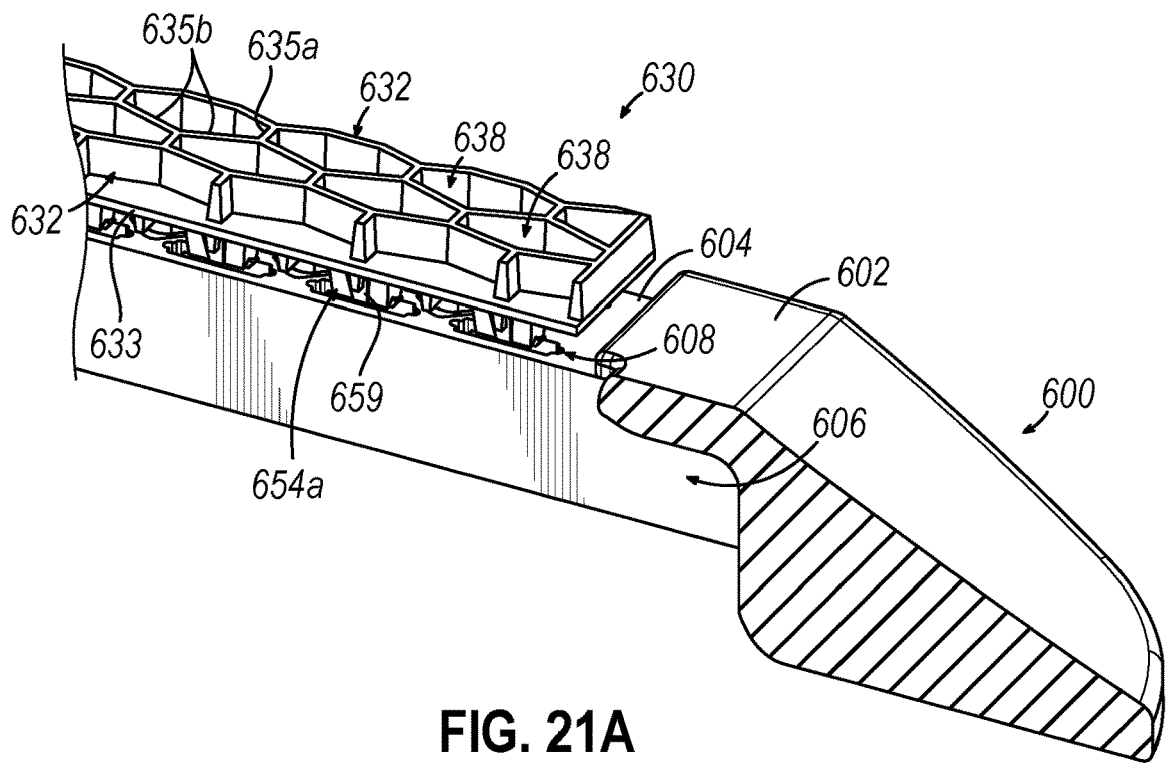
FIG. 21A depicts a side cross-sectional view of a portion of another exemplary staple cartridge in combination with another exemplary adjunct that has polygonal protrusions extending upwardly from a web for engaging tissue, and that further has pyramid-shaped protrusions extending downwardly from the web for engaging the staple cartridge, the pyramid-shaped protrusions including respective notches for receiving a crown of a corresponding staple deployed from the staple cartridge.
Figure 21B:
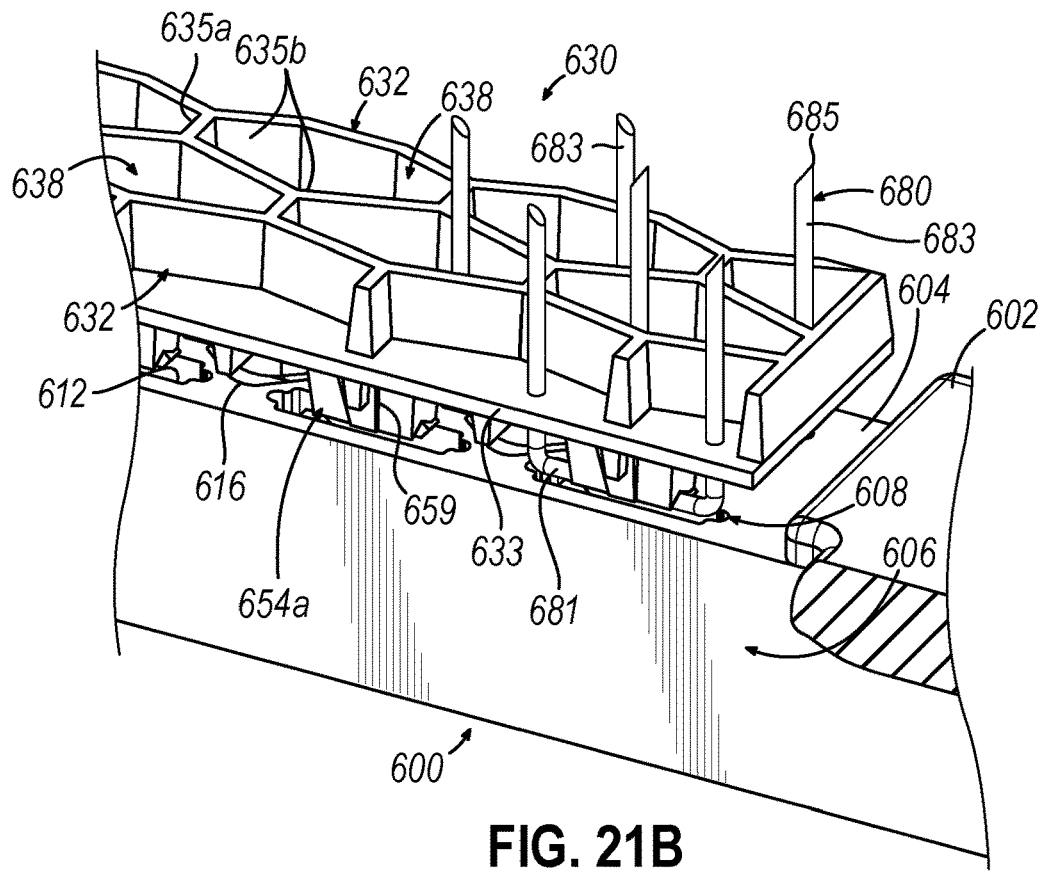
FIG. 21B depicts a magnified side cross-sectional view of the staple cartridge and adjunct of FIG. 21A, showing the web of the adjunct pierced by legs of the staples and further showing the crowns of the staples engaged with corresponding notches of the pyramid-shaped protrusions during deployment of the staples.

As best shown in FIG. 21B, each upper protrusion (632) partially overlies at least one corresponding lower protrusion (654a, 654b, 654c). More particularly, a longitudinal end (e.g., end wall (655a)) of each upper protrusion (632) overlies a longitudinally-central region of the at least one corresponding lower protrusion (654a, 654b, 654c). In this manner, the hollow interior of each upper protrusion (632) overlies a longitudinal end of the at least one corresponding lower protrusion (654a, 654b, 654c). For example, the hollow interiors of at least some upper protrusions (632) overlie a proximal end of a first corresponding lower protrusion (654a, 654b, 654c) and a distal end of a second corresponding lower protrusion (654a, 654b, 654c) that is longitudinally adjacent to the first corresponding lower protrusion (654a, 654b, 654c).

Each protrusion (654a, 654b, 654c) of adjunct (630) is configured to overlie a corresponding recess (612, 616) and/or a corresponding staple opening (608) of staple cartridge (600) to enable the crown (681) of each staple (680) slidably housed within the respective staple opening (608) to engage the corresponding notches (658a, 658b, 658c) during deployment of staples (680). In some versions, protrusions (654a, 654b, 654c) are at least partially received within corresponding recesses (612, 616) to promote such overlying of protrusions (654a, 654b, 654c) relative to the corresponding recesses (612, 616) and/or staple openings (608).

More particularly, each inner protrusion (654a) may be at least partially received within a corresponding inner recess (612), each outer protrusion (654b) may be at least partially received within a corresponding outer recess, and each medial protrusion (654) may be at least partially received within a corresponding medial recess (616). Locking ramps (659) may each be angled to engage the corresponding recess (612, 616) and/or staple opening (608) to assist with releasably attaching adjunct (630) to staple cartridge (600). In some versions, bottom surfaces of stiffening ribs (657) may be configured to rest on deck (604) such that web (633) may be disposed at a predetermined height above deck (604) with predetermined portions of protrusions (654a, 654b, 654c) received within the corresponding recesses (612, 616) and/or staple openings (608).

In any event, such overlying of protrusions (654a, 654b, 654c) relative to the corresponding recesses (612, 616) and/or staple openings (608) may also enable the legs (683) of each staple (680) slidably housed within the respective staple opening (608) to flank the corresponding lower protrusion (654a, 654b, 654c) and the longitudinal end of the corresponding upper protrusion (632) during deployment of staples (680), as shown in FIG. 22B. In this manner, the deformed legs (683) of each staple (680) capture and compress the corresponding protrusion (654a, 654b, 654c) against the crown (681) thereof when staples (680) are formed by staple forming pockets (58) of anvil (56). Such flanking of protrusions (654a, 654b, 654c) by the legs (683) of the corresponding staples (680) may also enable at least some staples (680) to avoid piercing the corresponding protrusions (632, 654a, 654b, 654c) during deployment of staples (680). Rather, one or both legs (683) of each staple (680) may pierce through web (633) adjacent to the corresponding protrusions (632, 654a, 654b, 654c). It will be appreciated that by receiving crowns (681) of the corresponding staples (680), notches (658a, 658b, 658c) may inhibit slipping of staples (680) relative to the corresponding protrusions (654a, 654b, 654c) and thereby assist with proper flanking of protrusions (654a, 654b, 654c) by staples (680). In addition, or alternatively, the piercing of legs (683) of staples (680) through web (633) may inhibit slipping of staples (680) relative to the corresponding protrusions (654a, 654b, 654c) and thereby assist with proper flanking of protrusions (654a, 654b, 654c) by staples (680). In some versions, adjunct (630) may be configured to provide a stress plateau when compressed for optimally compressing the stapled tissue over a predefined range of tissue thicknesses.

E. Exemplary Compressible Adjunct with Projections for Engaging Staple Openings

Figure 23:
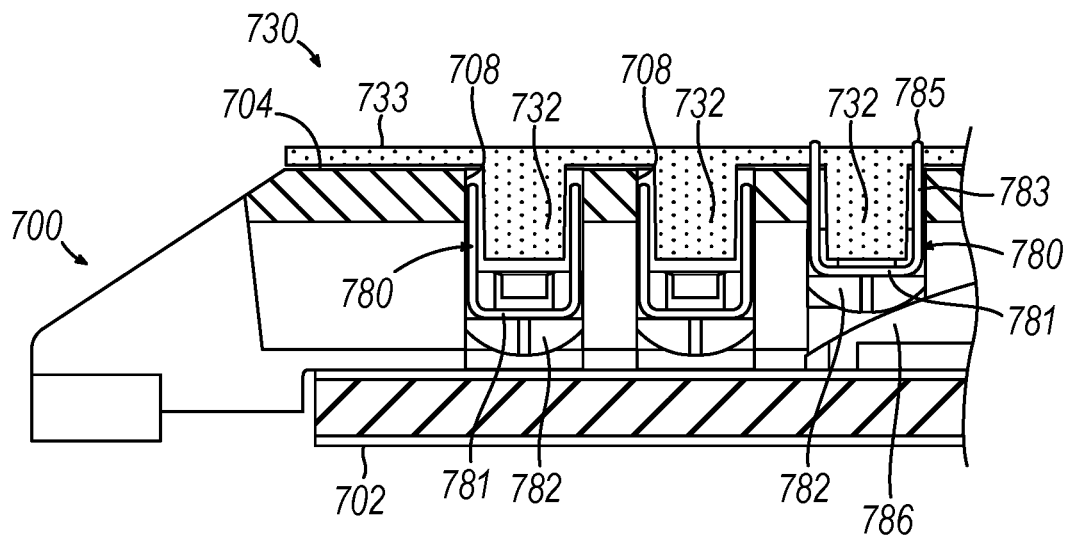
FIG. 23 depicts a side cross-sectional view of a portion of another exemplary staple cartridge in combination with another exemplary adjunct that has a plurality of foam protrusions extending downwardly from a foam base for engaging respective staple openings of the staple cartridge to brace the corresponding staples slidably housed therein.
Figure 24:
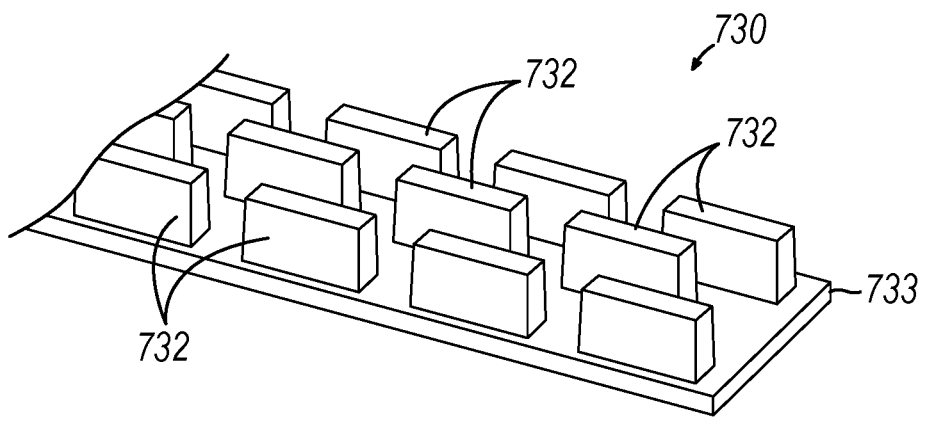
FIG. 24 depicts a bottom perspective view of the adjunct of FIG. 23.

FIGS. 23-24 show another exemplary compressible adjunct (730) configured for releasable attachment to a staple cartridge (700). Staple cartridge (700) and adjunct (730) are configured for use with end effector (50) and are similar to staple cartridge (200) and adjunct (230) described above except as otherwise described below. In this regard, staple cartridge (700) includes a cartridge body (702) having an upwardly facing deck (704), an elongate slot (not shown) extending along a central axis of cartridge body (702) and opening upwardly through deck (704), and a plurality of staple openings (708) extending through deck (704) on each side of the elongate slot. Each staple opening (708) slidably houses an unformed staple (780), and a respective staple driver (782) configured to drive the corresponding staple (780) outwardly toward anvil (56) to be formed. A lower tray (not shown) of staple cartridge (700) retains staples (780) and staple drivers (782) within cartridge body (702). A wedge sled (786) is slidably disposed within cartridge body (702) and includes upwardly presented cam surfaces configured to engage the undersides of staple drivers (782). Each staple (780) includes an elongate crown (781) and a pair of legs (783) extending upwardly and generally perpendicularly from respective ends of crown (781) to respective sharp tips (785).

Adjunct (730) of the present example has a plurality of staple leg constraints in the form of shape memory foam protrusions (732) extending downwardly from a shape memory foam base (733) of adjunct (730) for engaging respective staple openings (708) of staple cartridge (700). In the example shown, each protrusion (732) may serve as a brace for the staple (730) slidably housed within the respective staple opening (708) by resisting longitudinally-inner movement of the corresponding legs (783) as staples (780) are driven outwardly from staple openings (708) by staple drivers (782). In some versions, adjunct (730) including protrusions (732) may be configured to be released from deck (704) and deployed with staples (780).

In this regard, adjunct (730) may be formed of an elastic, bioabsorbable polymeric (e.g., elastomeric) material having a suitable degree of elasticity that enables adjunct (730) to compress and resiliently resume its original shape, while having a suitable degree of stiffness for resisting longitudinal compression of protrusions (732) by legs (783) as staples (780) are driven outwardly from staple openings (708) by staple drivers (782). In some versions, base (733) may have a higher density than protrusions (732) and thereby constrain legs (783) laterally and longitudinally for vertically guiding legs (783) out of the respective staple opening (708) toward the corresponding staple forming pockets (58) as staples (780) are driven outwardly from staple openings (708) by staple drivers (782). In addition, or alternatively, base (733) may be constructed of a relatively stiff foam having a relatively high glass transition temperature, while protrusions (732) may each be constructed of a relatively soft foam having a relatively low glass transition temperature.

In some versions, protrusions (732) may each be substantially wider than the respective staple openings (708) such that each protrusion (732) may be substantially compressed to fit therein. Thus, protrusions (732) may expand significantly (e.g., in the lateral direction) during deployment. For example, each protrusion (732) may be wider than the corresponding crown (781) after deployment. In addition, or alternatively, protrusions (732) may provide adjunct (730) with an increased initial thickness after deployment, at least by comparison to adjuncts lacking such protrusions. In this regard, housing protrusions (732) within staple openings (708) prior to deployment may enable a decrease in the thickness of base (733) on deck (704), such that deck (704) may be raised, thereby enabling increased heights of staples (780), increased thicknesses of deck (704), and/or increased thicknesses of staple drivers (482), for example.

F. Exemplary Mesh Adjunct with Projections for Engaging Staple Openings

Figure 25:
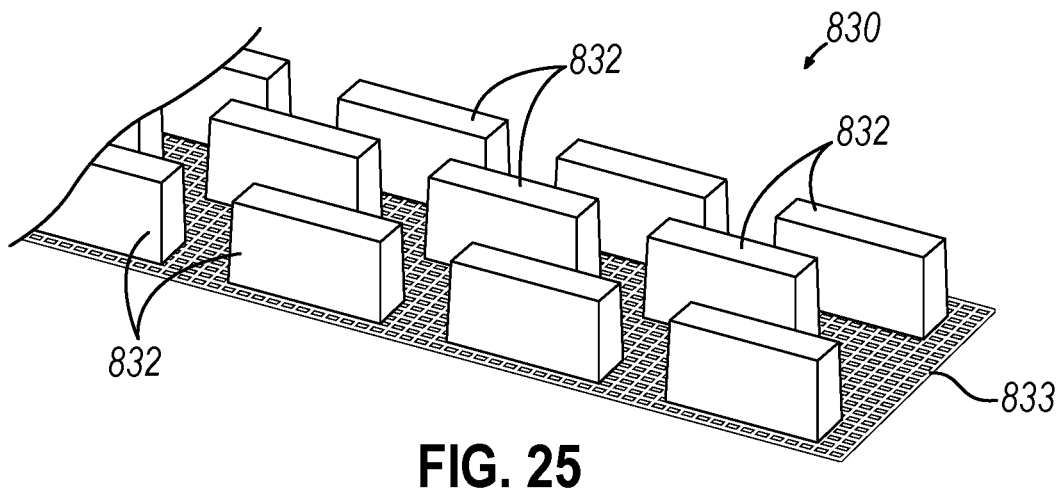
FIG. 25 depicts a bottom perspective view of another exemplary adjunct that has a plurality of foam protrusions extending downwardly from a mesh base for engaging respective staple openings of a staple cartridge to brace the corresponding staples slidably housed therein.

FIG. 25 shows another exemplary compressible adjunct (830) configured for releasable attachment to a staple cartridge (not shown) similar to staple cartridge (200). Adjunct (830) is configured for use with end effector (50) and is similar to adjunct (730) described above except as otherwise described below. In this regard, adjunct (830) has a plurality of shape memory foam protrusions (832) extending downwardly from a woven matrix or mesh base (833) of adjunct (830) for engaging respective staple openings of the staple cartridge. Mesh base (833) may be generally similar to buttress bodies (114, 118) described above.

G. Exemplary Wedge Sled with Tissue-Lifting Fin Member

Figure 26:
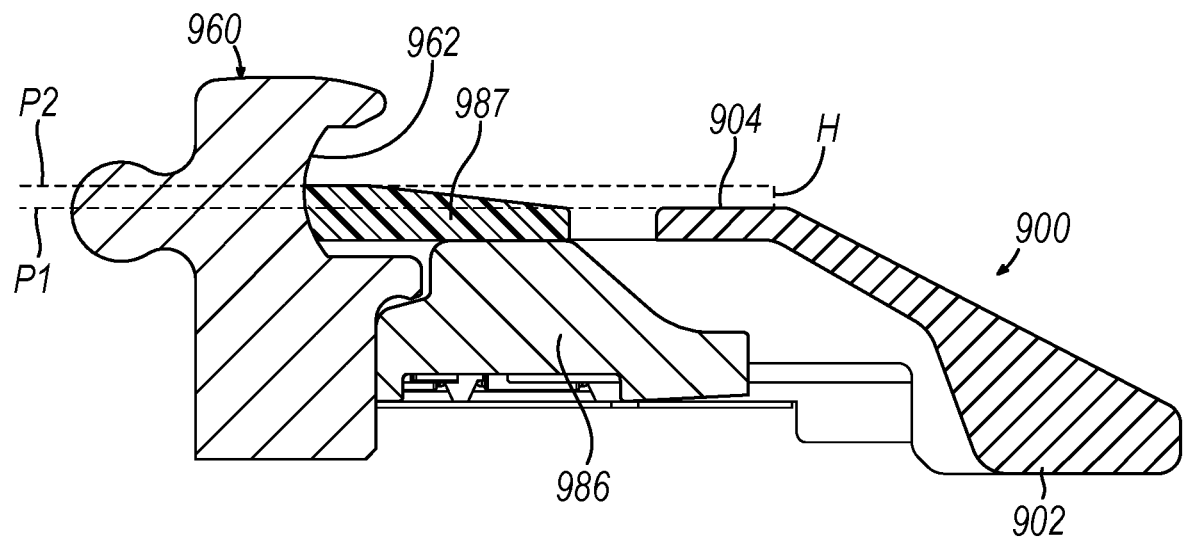
FIG. 26 depicts a side cross-sectional view of a portion of another exemplary staple cartridge having a wedge sled with a fin member for lifting tissue above a deck of the staple cartridge.
Figure 27:
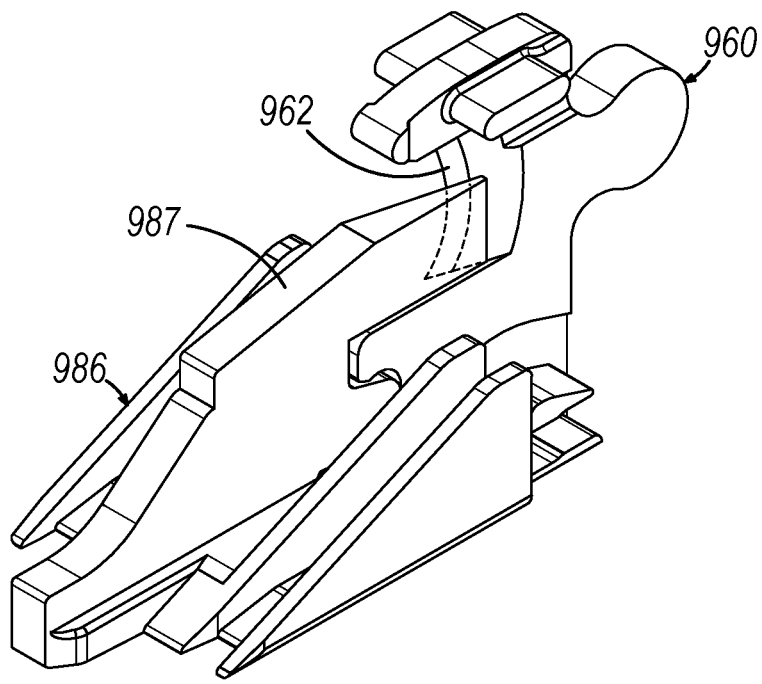
FIG. 27 depicts a perspective view of the wedge sled of FIG. 26.

FIGS. 26-27 show another exemplary staple cartridge (900) configured to deploy staples (not shown). Staple cartridge (900) is configured for use with end effector (50) and is similar to staple cartridge (200) described above except as otherwise described below. In this regard, staple cartridge (900) includes a cartridge body (902) having an upwardly facing deck (904), an elongate slot (not shown) extending along a central axis of cartridge body (902) and opening upwardly through deck (904), and a plurality of staple openings (not shown) extending through deck (904) on each side of the elongate slot. Each staple opening slidably houses an unformed staple (not shown), and a respective staple driver (not shown) configured to drive the corresponding staple outwardly toward anvil (56) to be formed. A wedge sled (986) is slidably disposed within cartridge body (902) and includes upwardly presented cam surfaces configured to engage the undersides of the staple drivers when wedge sled (986) is driven distally by the distal end of a firing member (960), which is configured to simultaneously cut tissue with a distally presented cutting edge (962).

Wedge sled (986) of the present example includes a fin member (987) for lifting tissue (and/or an adjunct) above deck (904) from a first plane (P1) defined by deck (904) toward a second plane (P2) at a height (H) above deck (904). In this regard, cutting edge (962) may provide optimal cutting of tissue when such tissue is disposed at second plane (P2). In some versions, fin member (987) is an integral component of wedge sled (986). In other versions, fin member (987) may be formed separately from wedge sled (986) and coupled thereto. In the example shown, fin member (987) is blunt and is defined by a sloped surface. It will be appreciated that fin member (987) may be sharp for severing tissue. For example, fin member (987) may be configured as a curved blade and may apply pressure against a lateral side of firing member (960) near cutting edge (962) to provide a shearing action through tissue (and/or an adjunct).

H. Exemplary Bioabsorbable Springs for Bracing Staples

Figure 28:
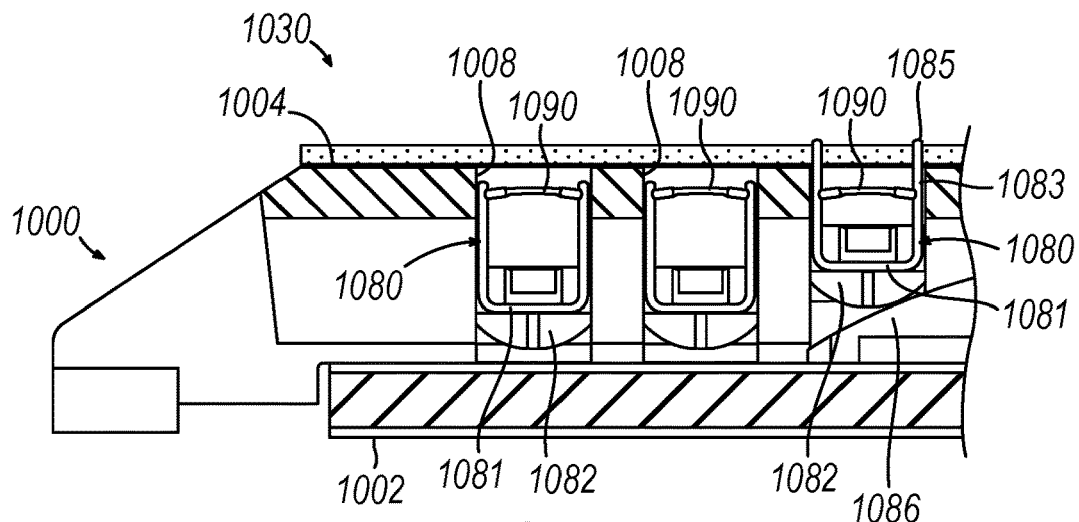
FIG. 28 depicts a side cross-sectional view of a portion of another exemplary staple cartridge in combination with another exemplary adjunct, showing a plurality of compression springs bracing corresponding staples slidably housed within respective staple openings of the staple cartridge.
Figure 29:
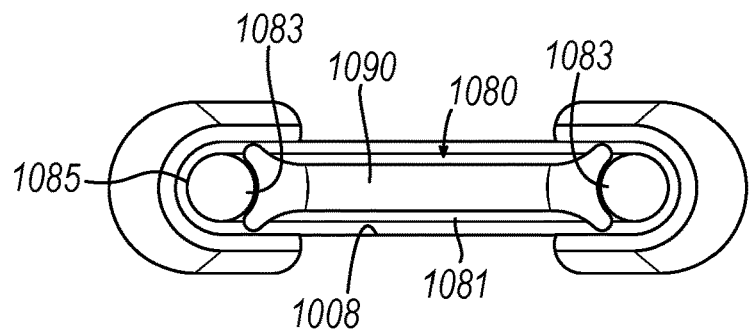
FIG. 29 depicts a top plan view of one of the staple openings of the staple cartridge of FIG. 28, showing the corresponding compression spring resisting longitudinally-inner movement of the respective staple legs toward each other.
Figure 30:
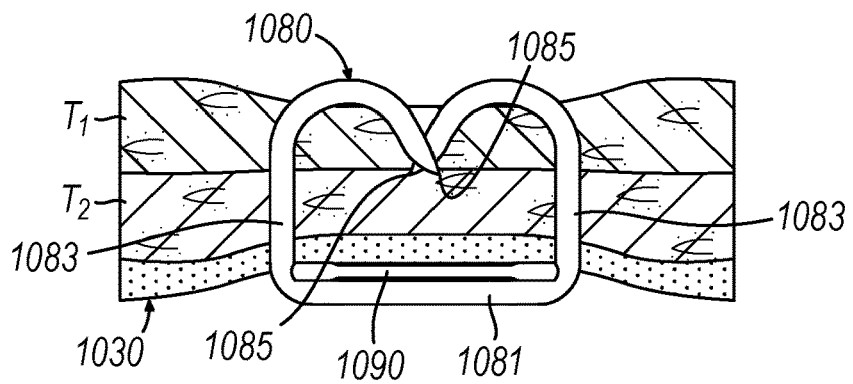
FIG. 30 depicts a cross-sectional view of a formed staple and the adjunct of FIG. 28 after having been secured to the tissue by the end effector of FIG. 3, showing the corresponding compression spring captured between a crown of the staple and the adjunct.

FIGS. 28-30 show another exemplary compressible adjunct (1030) configured for releasable attachment to a staple cartridge (1000). Staple cartridge (1000) and adjunct (1030) are configured for use with end effector (50) and are similar to staple cartridge (200) and adjunct (230) described above except as otherwise described below. In this regard, staple cartridge (1000) includes a cartridge body (1002) having an upwardly facing deck (1004), an elongate slot (not shown) extending along a central axis of cartridge body (1002) and opening upwardly through deck (1004), and a plurality of staple openings (1008) extending through deck (1004) on each side of the elongate slot. Each staple opening (1008) slidably houses an unformed staple (1080), and a respective staple driver (1082) configured to drive the corresponding staple (1080) outwardly toward anvil (56) to be formed. A lower tray (not shown) of staple cartridge (1000) retains staples (1080) and staple drivers (1082) within cartridge body (1002). A wedge sled (1086) is slidably disposed within cartridge body (1002) and includes upwardly presented cam surfaces configured to engage the undersides of staple drivers (1082). Each staple (1080) includes an elongate crown (1081) and a pair of legs (1083) extending upwardly and generally perpendicularly from respective ends of crown (1081) to respective sharp tips (1085).

In the example shown, a plurality of staple leg constraints in the form of compression springs (1090) are compressed between legs (1083) of corresponding staples (1080) near the respective tips (1085) thereof to serve as braces for the corresponding staples by resisting longitudinally-inner movement of the corresponding legs (1083) as staples (1080) are driven outwardly from staple openings (1008) by staple drivers (1082). In some versions, springs (1090) may be configured to be deployed with staples (1080). For example, springs (1090) may be captured between the corresponding crown (1081) and the stapled tissue layers ($T_1$, $T_2$) and/or between the corresponding crown (1081) and adjunct (1030), as shown in FIG. 30. In this regard, springs (1090) may each be constructed of any suitable bioabsorbable materials.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an end effector including: (i) a first jaw having a plurality of pockets, and (ii) a second jaw, wherein the first and second jaws are operable to clamp tissue therebetween; (b) a stapling assembly supported by the second jaw of the end effector, wherein the stapling assembly includes: (i) a deck, (ii) a plurality of staple openings extending through the deck, and (iii) a plurality of staples slidably housed within corresponding staple openings of the plurality of staple openings, wherein each staple of the plurality of staples has a respective pair of legs configured to be driven into contact with a corresponding pocket of the plurality of pockets; and (c) a plurality of staple leg constraints, wherein each staple leg constraint of the plurality of staple leg constraints is aligned with and extends at least partially across a corresponding staple opening of the plurality of staple openings for guiding a respective leg of the corresponding staple toward the corresponding pocket of the plurality of pockets.

Example 2

The surgical instrument of Example 1, wherein each staple opening of the plurality of staple openings includes a proximal end and a distal end, wherein the plurality of staple leg constraints includes a proximal staple leg constraint extending at least partially across the corresponding staple opening near the respective proximal end, and a distal staple leg constraint extending at least partially across the corresponding staple opening near the respective distal end.

Example 3

The surgical instrument of any one or more of Examples 1 through 2, wherein each staple leg constraint of the plurality of staple leg constraints is flexible.

Example 4

The surgical instrument of any one or more of Examples 1 through 3, wherein each staple of the plurality of staples has a respective crown extending between the respective pair of legs, wherein each staple leg constraint of the plurality of staple leg constraints extends at least partially over the respective crown of the corresponding staple.

Example 5

The surgical instrument of any one or more of Examples 1 through 4, wherein each staple leg constraint of the plurality of staple leg constraints is configured to resist lateral movement of the respective leg.

Example 6

The surgical instrument of any one or more of Examples 1 through 5, wherein each staple leg constraint of the plurality of staple leg constraints is configured to resist longitudinal movement of the respective leg.

Example 7

The surgical instrument of any one or more of Examples 1 through 6, wherein each staple leg constraint of the plurality of staple leg constraints includes a pocket extending member extending upwardly from the deck.

Example 8

The surgical instrument of any one or more of Examples 1 through 7, wherein each staple leg constraint of the plurality of staple leg constraints is configured to be deployed from the stapling assembly.

Example 9

The surgical instrument of Example 8, wherein each staple leg constraint of the plurality of staple leg constraints includes a bioabsorbable polymeric material.

Example 10

The surgical instrument of any one or more of Examples 8 through 9, wherein each staple leg constraint of the plurality of staple leg constraints includes a suture strand strung laterally across the deck.

Example 11

The surgical instrument of any one or more of Examples 8 through 10, further comprising an adjunct releasably secured to the deck, wherein each staple leg constraint of the plurality of staple leg constraints is presented by the adjunct.

Example 12

The surgical instrument of Example 11, wherein the adjunct includes a base, wherein each staple leg constraint of the plurality of staple leg constraints includes a bore extending through the base.

Example 13

The surgical instrument of Example 11, wherein the adjunct includes a base, wherein each staple leg constraint of the plurality of staple leg constraints includes at least a portion of a protrusion extending downwardly from the base.

Example 14

The surgical instrument of Example 13, wherein each staple of the plurality of staples has a respective crown extending between the respective pair of legs, wherein the at least one protrusion includes at least one notch for receiving the respective crown of the corresponding staple.

Example 15

The surgical instrument of any one or more of Examples 13 through 14, wherein the at least one protrusion is resiliently compressible.

Example 16

An adjunct configured for use with an end effector of a surgical stapler, comprising: (a) a base configured to be removably secured to a jaw of the end effector; (b) a plurality of resiliently compressible protrusions interconnected with each other via the base, wherein each resiliently compressible protrusion of the plurality of resiliently compressible protrusions has a hollow interior; and (c) at least one staple leg constraint, wherein the at least one staple leg constraint is configured to vertically guide a respective leg of a corresponding staple ejected from the end effector into tissue clamped by the end effector, wherein each resiliently compressible protrusion of the plurality of resiliently compressible protrusions is configured to be captured and compressed by the corresponding staple ejected from the end effector into the clamped tissue and thereby reinforce the engagement between the ejected staples and the clamped tissue.

Example 17

The adjunct of Example 16, wherein the at least one staple leg constraint includes at least one bore extending through the base.

Example 18

The adjunct of Example 16, wherein the at least one staple leg constraint includes at least one wall of at least one protrusion of the plurality of resiliently compressible protrusions.

Example 19

The adjunct of any one or more of Examples 16 through 18, wherein at least one protrusion of the plurality of resiliently compressible protrusions includes at least one notch for receiving a respective crown of the corresponding staple ejected from the end effector into the clamped tissue.

Example 20

An adjunct configured for use with an end effector of a surgical stapler, comprising: (a) a base configured to be removably secured to a jaw of the end effector; and (b) a plurality of bores extending through the base, wherein the base is configured to contact tissue clamped by the end effector during closure thereof, wherein the base is further configured to be captured by staples ejected from the end effector into the clamped tissue and thereby reinforce the engagement between the ejected staples with the clamped tissue, wherein each bore of the plurality of bores is configured to vertically guide a respective leg of a corresponding staple ejected from the end effector into the clamped tissue.

VI. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/704,075, entitled "Tissue Cushion Adjuncts for Surgical Stapler End Effector," filed on Mar. 25, 2022, published as U.S. Pub. No. 2023/0301656 on Sep. 28, 2023; U.S. patent application Ser. No. 17/704,079, entitled "Tissue Cushion Adjunct for Surgical Stapler End Effector," filed on Mar. 25, 2022, published as U.S. Pub. No. 2023/0301674 on Sep. 28, 2023; U.S. patent application Ser. No. 17/704,082, entitled "Thermally Formed Tissue Cushion Adjunct for Surgical Stapler End Effector," filed on Mar. 25, 2022, published as U.S. Pub. No. 2023/0301657 on Sep. 28, 2023; and U.S. patent application Ser. No. 17/704,094, entitled "Surgical Stapler Features for Stapling Variable Thickness Tissue," filed on Mar. 25, 2022, published as U.S. Pub. No. 2023/0301675 on Sep. 28, 2023. The disclosure of each of these U.S. patent references is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) an end effector including:
      (i) a first jaw having a plurality of pockets, and
      (ii) a second jaw, wherein the first and second jaws are operable to clamp tissue therebetween;
   (b) a stapling assembly supported by the second jaw of the end effector, wherein the stapling assembly includes:
      (i) a deck,
      (ii) a plurality of staple openings extending through the deck, and
      (iii) a plurality of staples slidably housed within corresponding staple openings of the plurality of staple openings, wherein each staple of the plurality of staples has a respective pair of legs configured to be driven into contact with a corresponding pocket of the plurality of pockets; and (c) a plurality of staple leg constraints, wherein each staple leg constraint of the plurality of staple leg constraints is aligned with and extends at least partially across a corresponding staple opening of the plurality of staple openings for guiding a respective leg of the corresponding staple toward the corresponding pocket of the plurality of pockets, wherein each staple leg constraint of the plurality of staple leg constraints is flexible, wherein each staple of the plurality of staples has a respective crown extending between the respective pair of legs, wherein each staple leg constraint of the plurality of staple leg constraints extends at least partially over the respective crown of the corresponding staple, wherein each staple leg constraint of the plurality of staple leg constraints is coupled to and extends upwardly from the deck.

2. The surgical instrument of claim 1, wherein each staple opening of the plurality of staple openings includes a proximal end and a distal end, wherein the plurality of staple leg constraints includes a proximal staple leg constraint extending at least partially across the corresponding staple opening near the respective proximal end, and a distal staple leg constraint extending at least partially across the corresponding staple opening near the respective distal end.

3. The surgical instrument of claim 1, wherein each staple leg constraint of the plurality of staple leg constraints is configured to resist lateral movement of the respective leg.

4. The surgical instrument of claim 1, wherein each staple leg constraint of the plurality of staple leg constraints is configured to resist longitudinal movement of the respective leg.

5. The surgical instrument of claim 1, wherein each staple leg constraint of the plurality of staple leg constraints includes a pocket extending member extending upwardly from the deck.

6. The surgical instrument of claim 1, wherein each staple leg constraint of the plurality of staple leg constraints includes a U-shaped body.

7. The surgical instrument of claim 6, wherein each U-shaped body defines a staple leg receptacle sized and configured to slidably receive the respective leg of the corresponding staple.

8. The surgical instrument of claim 1, wherein each staple leg constraint of the plurality of staple leg constraints comprises an elastic material.

9. The surgical instrument of claim 1, wherein each staple leg constraint of the plurality of staple leg constraints is configured to enhance gripping of the tissue by the stapling assembly.

10. A surgical instrument comprising:
(a) an end effector including:
  (i) a first jaw having a plurality of pockets, and
  (ii) a second jaw, wherein the first and second jaws are operable to clamp tissue therebetween;
(b) a stapling assembly supported by the second jaw of the end effector, wherein the stapling assembly includes:
  (i) a deck,
  (ii) a plurality of staple openings extending through the deck, and
  (iii) a plurality of staples slidably housed within corresponding staple openings of the plurality of staple openings, wherein each staple of the plurality of staples has a respective pair of legs configured to be driven into contact with a corresponding pocket of the plurality of pockets; and
(c) a plurality of staple leg constraints, wherein each staple leg constraint of the plurality of staple leg constraints is aligned with and extends at least partially across a corresponding staple opening of the plurality of staple openings for guiding a respective leg of the corresponding staple toward the corresponding pocket of the plurality of pockets, wherein each staple leg constraint of the plurality of staple leg constraints is flexible, wherein each staple of the plurality of staples has a respective crown extending between the respective pair of legs, wherein each staple leg constraint of the plurality of staple leg constraints extends at least partially over the respective crown of the corresponding staple, wherein each staple leg constraint of the plurality of staple leg constraints is configured to remain coupled to the deck following deployment of the corresponding staple from the corresponding staple opening.

11. A surgical instrument comprising:
(a) an end effector including:
  (i) a first jaw having a plurality of pockets, and
  (ii) a second jaw, wherein the first and second jaws are operable to clamp tissue therebetween;
(b) a stapling assembly supported by the second jaw of the end effector, wherein the stapling assembly includes:
  (i) a deck,
  (ii) a plurality of staple openings extending through the deck, and
  (iii) a plurality of staples slidably housed within corresponding staple openings of the plurality of staple openings, wherein each staple of the plurality of staples has a respective pair of legs configured to be driven into contact with a corresponding pocket of the plurality of pockets; and
(c) a plurality of staple leg constraints, wherein each staple leg constraint of the plurality of staple leg constraints is aligned with and extends at least partially across a corresponding staple opening of the plurality of staple openings for guiding a respective leg of the corresponding staple toward the corresponding pocket of the plurality of pockets, wherein each staple leg constraint of the plurality of staple leg constraints is flexible, wherein each staple of the plurality of staples has a respective crown extending between the respective pair of legs, wherein each staple leg constraint of the plurality of staple leg constraints extends at least partially over the respective crown of the corresponding staple, wherein each staple leg constraint of the plurality of staple leg constraints includes a pair of laterally-opposed detents extending laterally toward each other.

12. The surgical instrument of claim 11, wherein the detents of each pair of laterally-opposed detents are spaced apart from each other to define an expandable constriction.

13. The surgical instrument of claim 12, wherein each expandable constriction is configured to be laterally expanded by the respective crown of the corresponding staple to permit vertical passage of the respective crown of the corresponding staple therethrough.

14. The surgical instrument of claim 11, wherein the detents of each pair of laterally-opposed detents are configured to be urged laterally away from each other by the respective crown of the corresponding staple.

15. A surgical instrument comprising:
(a) an end effector including:
(i) a first jaw having a plurality of pockets, and
(ii) a second jaw, wherein the first and second jaws are operable to clamp tissue therebetween;
(b) a stapling assembly supported by the second jaw of the end effector, wherein the stapling assembly includes:
(i) a deck,
(ii) a plurality of staple openings extending through the deck, and
(iii) a plurality of staples slidably housed within corresponding staple openings of the plurality of staple openings, wherein each staple of the plurality of staples has:
(A) a respective pair of legs configured to be driven into contact with a corresponding pocket of the plurality of pockets, and
(B) a respective crown extending between the respective pair of legs; and
(c) a plurality of staple leg constraints coupled to and extending upwardly from the deck, wherein each staple leg constraint of the plurality of staple leg constraints is configured to guide a respective leg of a corresponding staple of the plurality of staples toward the corresponding pocket of the plurality of pockets, wherein each staple leg constraint of the plurality of staple leg constraints extends at least partially over the respective crown of the corresponding staple.

16. The surgical instrument of claim 15, wherein each staple leg constraint of the plurality of staple leg constraints includes a pocket extending member extending upwardly from the deck.

17. The surgical instrument of claim 16, wherein each pocket extending member is flexible.

18. A surgical instrument comprising:
(a) an end effector including:
(i) a first jaw having a pocket, and
(ii) a second jaw, wherein the first and second jaws are operable to clamp tissue therebetween;
(b) a stapling assembly supported by the second jaw of the end effector, wherein the stapling assembly includes:
(i) a deck,
(ii) a staple opening extending through the deck, wherein the staple opening includes a proximal end and a distal end, and
(iii) a staple slidably housed within the staple opening, wherein the staple has a proximal leg and a distal leg, wherein the proximal and distal legs are configured to be driven into contact with the pocket;
(c) a proximal staple leg constraint extending at least partially across the staple opening near the proximal end of the staple opening and at least partially over a crown of the staple for guiding the proximal leg of the staple toward the pocket; and
(d) a distal staple leg constraint extending at least partially across the staple opening near the distal end of the staple opening and at least partially over the crown for guiding the distal leg of the staple toward the pocket, wherein at least one of the proximal staple leg constraint or the distal staple leg constraint is coupled to and extends upwardly from the deck.

19. The surgical instrument of claim 18, wherein the proximal and distal staple leg constraints include proximal and distal pocket extending members extending upwardly from the deck, respectively.

20. The surgical instrument of claim 18, wherein the at least one of the proximal staple leg constraint or the distal staple leg constraint is configured to remain coupled to the deck following driving of the proximal and distal legs into contact with the pocket.

* * * * *